(12) United States Patent
Higgins et al.

(10) Patent No.: US 9,757,021 B2
(45) Date of Patent: Sep. 12, 2017

(54) GLOBAL AND SEMI-GLOBAL REGISTRATION FOR IMAGE-BASED BRONCHOSCOPY GUIDANCE

(75) Inventors: William E. Higgins, State College, PA (US); Rahul Khare, State College, PA (US)

(73) Assignee: The Penn State Research Foundation, University Park, PA (US)

( * ) Notice: Subject to any disclaimer, the term of this patent is extended or adjusted under 35 U.S.C. 154(b) by 389 days.

(21) Appl. No.: 13/362,252

(22) Filed: Jan. 31, 2012

(65) Prior Publication Data
US 2012/0203065 A1 Aug. 9, 2012

Related U.S. Application Data

(60) Provisional application No. 61/439,536, filed on Feb. 4, 2011.

(51) Int. Cl.
*A61B 1/04* (2006.01)
*A61B 1/00* (2006.01)
(Continued)

(52) U.S. Cl.
CPC ............ *A61B 1/2676* (2013.01); *A61B 5/066* (2013.01); *A61B 6/12* (2013.01); *A61B 6/5217* (2013.01);
(Continued)

(58) Field of Classification Search
CPC ......... G06T 7/0012; G06T 2207/10081; G06T 7/0083; G06T 2207/30004; G06T 7/0081; G06T 2207/10072; G06T 2207/10088; G06T 7/0028; G06T 7/0038; G06T 2207/30096; G06T 2207/30061;
(Continued)

(56) References Cited

U.S. PATENT DOCUMENTS 7,983,459 B2 * 7/2011 Begelman et al. ............ 382/128
8,019,140 B2 * 9/2011 Odry et al. .................... 382/131
(Continued)

FOREIGN PATENT DOCUMENTS

JP 2000135215 A 5/2000

OTHER PUBLICATIONS

International Search Report and Written Opinion of co-pending application No. PCT/US2012/023297.
(Continued)

*Primary Examiner* — John P Leubecker
*Assistant Examiner* — Arnaldo Torres Diaz
(74) *Attorney, Agent, or Firm* — Dinsmore & Shohl LLP

(57) ABSTRACT

Two system-level bronchoscopy guidance solutions are presented. The first incorporates a global-registration algorithm to provide the physician with updated navigational and guidance information during bronchoscopy. The system can handle general navigation to a region of interest (ROI), as well as adverse events, and it requires minimal commands so that it can be directly controlled by the physician. The second solution visualizes the global picture of all the bifurcations and their relative orientations in advance and suggests the maneuvers needed by the bronchoscope to approach the ROI. Guided bronchoscopy results using human airway-tree phantoms demonstrate the potential of the two solutions.

19 Claims, 17 Drawing Sheets

(51) Int. Cl.
| | |
|---|---|
| A61B 1/267 | (2006.01) |
| A61B 5/06 | (2006.01) |
| A61B 6/12 | (2006.01) |
| A61B 6/00 | (2006.01) |
| G06K 9/00 | (2006.01) |
| G06K 9/03 | (2006.01) |
| G06K 9/62 | (2006.01) |
| A61B 90/00 | (2016.01) |

(52) U.S. Cl.
CPC ............ *A61B 6/5247* (2013.01); *A61B 6/583* (2013.01); *G06K 9/00208* (2013.01); *G06K 9/00214* (2013.01); *G06K 9/03* (2013.01); *G06K 9/6206* (2013.01); *A61B 2090/365* (2016.02)

(58) Field of Classification Search
CPC ................. G06T 7/0042; G06T 7/0024; G06T 2207/10068; G06T 2207/30064; G06T 2207/10076; G06T 2207/30021; G06T 2207/10104; G06T 2207/10108; G06T 7/004; G06T 7/0022; G06T 7/0032; G06T 7/0046; G06T 7/0065; G06T 2207/10101; G06T 7/0048; A61B 5/055; A61B 1/00009; A61B 1/0005; A61B 1/04; A61B 1/042; A61B 1/05; A61B 2017/00694; A61B 1/00096
See application file for complete search history.

(56) References Cited

U.S. PATENT DOCUMENTS

| | | | | |
|---|---|---|---|---|
| 8,139,836 | B2* | 3/2012 | Arnold et al. | 382/131 |
| 8,494,245 | B2* | 7/2013 | Liao et al. | 382/131 |
| 2003/0233099 | A1* | 12/2003 | Danaek et al. | 606/96 |
| 2005/0020878 | A1* | 1/2005 | Ohnishi et al. | 600/117 |
| 2005/0182295 | A1* | 8/2005 | Soper et al. | 600/117 |
| 2006/0149134 | A1* | 7/2006 | Soper et al. | 600/182 |
| 2007/0015997 | A1* | 1/2007 | Higgins et al. | 600/407 |
| 2007/0055128 | A1* | 3/2007 | Glossop | 600/407 |
| 2007/0118184 | A1* | 5/2007 | Danek et al. | 607/42 |
| 2008/0183073 | A1* | 7/2008 | Higgins et al. | 600/425 |
| 2008/0207997 | A1* | 8/2008 | Higgins et al. | 600/114 |
| 2010/0034449 | A1* | 2/2010 | Averbuch et al. | 382/131 |
| 2010/0041949 | A1* | 2/2010 | Tolkowsky | 600/109 |
| 2011/0065982 | A1* | 3/2011 | Wibowo et al. | 600/101 |
| 2011/0184238 | A1* | 7/2011 | Higgins et al. | 600/117 |
| 2011/0282151 | A1* | 11/2011 | Trovato et al. | 600/117 |
| 2012/0143029 | A1* | 6/2012 | Silverstein et al. | 600/374 |
| 2012/0158017 | A1* | 6/2012 | Naylor et al. | 606/130 |
| 2012/0230565 | A1* | 9/2012 | Steinberg et al. | 382/130 |
| 2012/0321159 | A1* | 12/2012 | Keller et al. | 382/131 |
| 2013/0034281 | A1* | 2/2013 | Strommer et al. | 382/128 |
| 2013/0063434 | A1* | 3/2013 | Miga et al. | 345/420 |
| 2013/0119984 | A1* | 5/2013 | Levy et al. | 324/309 |
| 2013/0158346 | A1* | 6/2013 | Soper et al. | 600/104 |
| 2013/0245432 | A1* | 9/2013 | Averbuch et al. | 600/424 |

OTHER PUBLICATIONS

Asano, F. et al., A virtual bronchoscopic navigation system for pulmonary peripheral lesions, *Chest*, 130(2):559-66, 2006.
Asano, F. et al., Diagnosis of peripheral pulmonary lesions using a bronchoscope insertion guidance system combined with endobronchial ultrasonography with a guide sheath, *Lung Cancer*, 60(3):366-373, 2008.
Asano, F., Virtual Bronchoscopic Navigation, *Clinics in Chest Medicine*, 31(1):75-85, 2010. Interventional Pulmonology.
Becker, H. et al., Bronchoscopic biopsy of peripheral lung lesions under electromagnetic guidance: A pilot study, *J. Bronchology*, 12(1):9-13, 2005.
Bricault, I. et al., Registration of Real and CT-Derived Virtual Bronchoscopic Images to Assist Transbronchial Biopsy, *IEEE Transactions on Medical Imaging*, 17(5):703-714, 1998.
Dolina, M. et al., Interbronchoscopist variability in endobronchial path selection: a simulation study, *Chest*, 133(4):897-905, 2008.
Gibbs, J. et al., 3D MDCT-based system for planning peripheral bronchoscopic procedures, *Computers in Biology and Medicine*, 39(3):266-279, 2009.
Gildea, R. et al., Electromagnetic navigation diagnostic bronchoscopy: a prospective study, *Am. J. Resp. Crit. Care Med.*, 174(9):982-989, 2006.
Graham, M. et al., Robust 3D Airway-Tree Segmentation for Image-Guided Peripheral Bronchoscopy, *IEEE Trans. Medical Imaging*, 29(4):982-997, 2010.
Helferty, J. et al., Computer-based system for the virtual-endoscopic guidance of bronchoscopy, *Comput. Vis. Image Underst.*, 108(1-2):171-187, 2007.
Higgins, W. et al., Integrated bronchoscopic video tracking and 3D CT registration for virtual bronchoscopy, *SPIE Medical Imaging 2003: Physiology and Function: Methods, Systems and Applications,*, 5031:80-89, 2003. A.V. Clough and A.A. Amini (ed.).
Higgins, W. et al., 3D CT-video fusion for image-guided bronchoscopy, *Comput. Med. Imaging Graph.*, 32(3):159-173, 2008.
Hopper, K. et al., Transbronchial biopsy with virtual CT bronchoscopy and nodal highlighting, *Radiology*, 221(2):531-536, 2001.
Jemal, A. et al., Cancer statistics, 2009, *CA Cancer J. Clin.*, 59(4):225-249, 2009.
Khare, R. et al., Toward image-based global registration for bronchoscopy guidance, *SPIE Medical Imaging 2010: Visualization, Image-Guided Procedures, and Modeling*, pp. 762510-1-762510-12, 2010.
McAdams, H. et al., Virtual bronchoscopy for directing transbronchial needle aspiration of hilar and mediastinal lymph nodes: a pilot study, *Am. J. Roentgenology*, 170(5):1361-1364, 1998.
Merritt, S. et al., Image-Guided Bronchoscopy for Peripheral Lung Lesions: A Phantom Study, *Chest*, 134(5):1017-1026, 2008.
Minami, H. et al., Interbronchoscopist variability in the diagnosis of lung cancer by flexible bronchoscopy, *Chest*, 105(2):1658-1662, 1994.
Mori, K. et al., Compensation of electromagnetic tracking system using an optical tracker and its application to bronchoscopy navigation system, SPIE, 6509: 65090M-1-12, 2007.
Nadeem, S., Fiberoptic bronchoscopy: the technique. educational material from Committee for European Education in Anesthesiology, http://www.euroviane.net, 2009.
Schwarz, Y. et al., Real-time electromagnetic navigation bronchoscopy to peripheral lung lesions using overlaid CT images: the first human study, *Chest*, 129(4):988-994, 2006.
Shinagawa, N. et al., Virtual bronchoscopic navigation system shortens the examination time—Feasibility study of virtual bronchoscopic navigation system, *Lung Cancer*, 56(2):201-206, 2007.
Sihoe, A. et al., Lung cancer staging, *J. Surgical Research*, 117(1):92-106, 2004.
Solomon, S. et al., Three-dimensionsal CT-guided bronchoscopy with a real-time electromagnetic position sensor: a comparison of two image registration methods, *Chest*, 118(6):1783-1787, 2000.
Soper, T. et al., Validation of CT-video registration for guiding a novel ultrathin bronchoscope to peripheral lung nodules using electromagnetic tracking, *Society of Photo-Optical Instrumentation Engineers (SPIE) Conference Series* in Society of Photo-Optical Instrumentation Engineers (SPIE) Conference Series, 2009.
Wegner, I. et al., Evaluation and extension of a navigation system for bronchoscopy inside human lungs, *SPIE Medical Imaging 2007: Visualization and Image-Guided Procedures*, pp. 65091H1-65091H12, 2007.

* cited by examiner

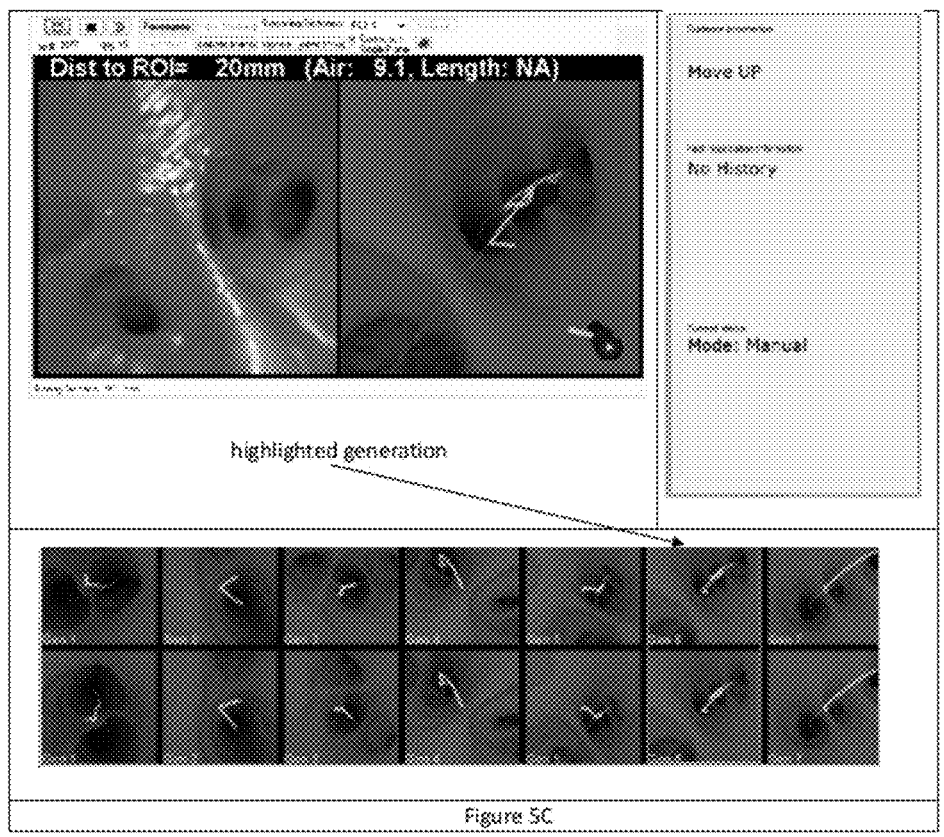

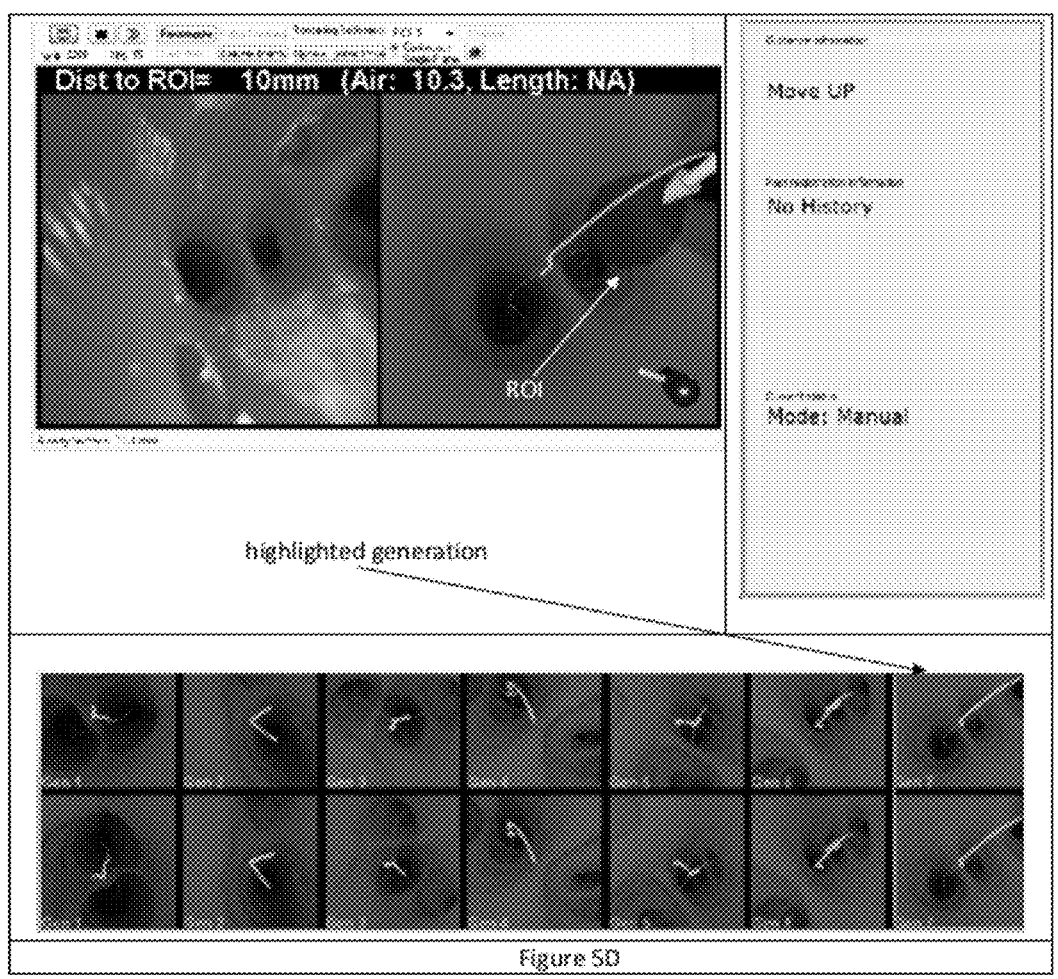

GLOBAL AND SEMI-GLOBAL REGISTRATION FOR IMAGE-BASED BRONCHOSCOPY GUIDANCE

REFERENCE TO REALTED APPLICATION

This application claims priority from U.S. Provisional patent application Ser. No. 61/439,536, filed Feb. 4, 2011, the entire content of which is incorporated herein by reference.

GOVERNMENT SPONSORSHIP

This invention was made with government support under Grant Nos. CA074325 and CA151433, awarded by the National Institutes of Health. The Government has certain rights in the invention.

FIELD OF THE INVENTION

This invention relates generally to image-based bronchoscopy guidance and, in particular, a global-registration algorithm that provides updated navigational and guidance information during bronchoscopy and a semi-global solution that draws upon a precomputed global picture of all bifurcation sites and associated bronchoscopy-friendly orientations along a preplanned route to a region of interest (ROI).

BACKGROUND OF THE INVENTION

Lung cancer is the leading cause of cancer death accounting for 30% of all male cancer deaths and 26% of all female cancer deaths in US in 2009 [1]. Bronchoscopy is a minimally invasive medical procedure used for staging lung cancer [2]. The standard lung-cancer assessment process involves two stages: 1) planning; and 2) live bronchoscopy [3]. During planning, the physician identifies diagnostic ROIs, such as lymph nodes and nodules using two-dimensional transverse slices from the three-dimensional (3D) multi-detector computed tomography (MDCT) chest scan of the patient. In this stage, the physician also mentally plans a 3D route through the airways to each ROI. Next, during bronchoscopy, the physician mentally registers the bronchoscope position in the 3D MDCT space using the video stream obtained from the bronchoscope. This manual approach to lung-cancer assessment, involving mental path-planning and registration, is well-known to be very difficult, resulting in large skill variations between physicians; also this approach results in navigation errors as early as the second airway generation [4,5].

Electromagnetic (EM) and image-based bronchoscopy guidance systems have been proposed to mitigate the navigational problems of standard bronchoscopy and to enable more effective bronchoscopy procedures [6-16]. EM-based bronchoscopy guidance systems consist of: a) a steerable EM sensor; b) an EM field generator; and c) guidance software [6,8-10,16]. The EM field generator is used to generate an EM field around the patient's chest. The steerable EM sensor, inserted through the bronchoscope's working channel to its tip, is tracked as it is maneuvered through the airways in the external EM field. Prior to the bronchoscopy procedure, the co-ordinate space of the EM field and the 3D MDCT co-ordinate space are synchronized. Thus, as the bronchoscope is moved through the airways, its global position in the MDCT co-ordinate space is nominally known. However, EM-based bronchoscopy guidance systems suffer from localization errors due to the patient's breathing motion; they also need considerable special hardware and are susceptible to local EM-field distortions [11, 12].

Image-based bronchoscopy guidance systems rely on volume-rendered or surface-rendered virtual bronchoscopic (VB) images of the endoluminal airway obtained from the 3D MDCT image [7,13-15,17-21]. During a procedure, the VB images are compared with the real bronchoscopic (RB) video frames, obtained from the camera at the tip of the bronchoscope, to establish the position of the bronchoscope in the airway tree. In the past, we proposed an image-based bronchoscopy guidance system that relied on discrete local registrations at consecutive bifurcations to guide the physician toward the ROI [13, 15]. This system has been extensively validated in live bronchoscopy and was found to suffer from the following limitations: 1) an attending technician must carefully follow the bronchoscope position; 2) it is unable to detect and correct faulty bronchoscope maneuvers, especially when the bronchoscope is advanced across multiple bifurcations; and 3) a re-synchronization procedure has to be followed after adverse events such as patient coughing.

SUMMARY OF THE INVENTION

This invention provides two related solutions to existing image-based bronchoscopy guidance. The first solution is a system-level guidance strategy that incorporates a global-registration algorithm to provide a physician with updated navigational and guidance information during bronchoscopy. This solution can detect faulty bronchoscope maneuvers and enables bronchoscopy guidance that can quickly recover after adverse events. The second semi-global solution draws upon a precomputed global picture of all bifurcation sites and associated bronchoscopy-friendly orientations along the preplanned route to an ROI. This solution guides the physician with discrete suggested bronchoscope maneuvers along the route to the ROI.

In a system for image-guided bronchoscopy, wherein global and local algorithms are used to register real bronchoscopic (RB) endoluminal video frames obtained from a bronchoscope to virtual bronchoscopic (VB) views computed from a 3D MDCT chest scan, this invention resides in a registration process. In broad and general terms, the process includes the steps of detecting faulty bronchoscope maneuvers, such maneuvers being defined as adverse events, and recovering from the adverse events. An adverse event may be defined as a cough or other event causing the bronchoscope to move to an unknown position within an airway tree.

As one example, a user may hold the bronchoscope steady until the adverse event passes. Alternatively, after the adverse event has elapsed, the bronchoscope may be moved to a nearby bifurcation so that the endoluminal video frames provide a complete view of the lumen region.

In the preferred embodiments, a global registration algorithm is invoked at every bifurcation to synchronize the positions of the real and virtual bronchoscopes. Once in the vicinity of a region of interest (ROI), the local registration algorithm may be invoked for synchronization purposes. The ROI may be superimposed on an RB frame along with a graphical arrow to localize the ROI.

The method may include the step of advancing the bronchoscope by one airway generation along an indicated path if it is determined that global registration is correct, and the bronchoscope is on the correct path. However, a user may pull back on the bronchoscope N generations, where N indicates the number of airway generations needed to pull the bronchoscope back onto the correct path, if it is determined that global registration is correct but that the bronchoscope is not on the correct path.

The method may include the step of holding the bronchoscope steady and causing the virtual bronchoscope to return to its previous position if it is determined that global registeration is incorrect when invoking the global registration algorithm. The system may be operated by a single user control, thereby allowing system control directly by physician without any need for technician.

The search space of the global registration algorithm may include branches lying within one or more airway generations about a previously registered position. Alternatively, the search space may be limited to a specific lung, a specific lobar region of a lung, or a user-defined parameter. The search space may be tuned to detect faulty maneuvers by a bronchoscope, or tuned to re-establish the position of the bronchoscope in an airway tree. Directions may be suggested to the physician other user at each bifurcation, including directions to move back to the correct route in case of faulty bronchoscope maneuvers or other adverse events.

A semi-global method for image-guided bronchoscopy according to the invention includes the step of presenting a global picture of all bifurcations and their relative proper orientations along a route to a region of interest (ROI) to guide a user to the ROI. The method may further include the use of a single user input, thereby allowing system control directly by a physician or other user.

The method may include the step of presenting two views for every bifurcation along the route to the ROI. One view may depict the bifurcation as seen by the bronchoscope when that bifurcation is approached by the bronchoscope, or one view may depict the bifurcation as seen by the bronchoscope after the suggested discrete bronchoscope maneuver is carried out. An animated sequence may be used to suggest a bronchoscope maneuver.

Standard bronchoscope maneuvers, such as the rotate-flex-advance maneuver, may be used to deteiinine the exact discrete maneuvers to be made by the bronchoscope at every bifurcation along the route to the ROI. Known limitations in the maneuverability of a bronchoscope within an airway tree may be used to determine the exact discrete bronchoscope maneuvers at every bifurcation along the route to the ROI. Bronchoscope rotation limitations due to the bronchoscope grip design may be incorporated in the calculation of discrete bronchoscope maneuvers suggested at every bifurcation along the route to the ROI. Precise discrete maneuvers may be calculated to minimize the total rotation of the bronchoscope for all the bifurcations along the route to the ROI.

User preferences for bifurcation orientations may be used to calculate the exact bronchoscope maneuvers at every bifurcation. An airway tree topology may be used to determine the exact discrete bronchoscope maneuvers at every bifurcation along the route to the ROI. Discrete bronchoscope rotation and articulation maneuvers may be suggested to the physician or other practitioner at each bifurcation. Branch length, orientation and airway tree topology may be used to determine bifurcations that can be skipped while presenting the global picture to guide a user to the ROI. The parameters used to determine a skipped bifurcation may be user-defined.

BRIEF DESCRIPTION OF THE DRAWINGS

FIGS. 1A-1D show visualization tools used for guided bronchoscopy; specifically, FIG. 1A displays a labeled segmented airway tree, the centerlines, the preplanned ROI route, ROI (a node at the end of the right intermediate bronchus) and the current virtual bronchoscope position;

FIG. 1B shows the CT-Video Match Tool which depicts two sections. The top section displays the current VB (right) and RB view (left) side-by-side. The lower section displays the frozen VB view (right) and the RB view (left) with the paths and ROI superimposed on it at the last registration;

FIG. 1C shows the thumbnail tool which depicts two sets of VB views at all encountered bifurcations along the preplanned ROI route with the correct route highlighted for every bifurcation. The top VB view depicts the bifurcation as seen when the bifurcation is approached by the bronchoscope. The bottom VB view depicts the bifurcation after the bronchoscope has been rotated as per the guidance instructions. The current bifurcation (second) is highlighted by an enclosing box;

FIG. 1D shows the guidance dialog which suggests to the physician the proper bronchoscope maneuver to be made at the second bifurcation along the ROI's route;

FIGS. 2A-2H depict the system display during image-guided bronchoscopy to an ROI (a lymph node at the end of the right intermediate bronchus);

FIG. 2A shows how the virtual bronchoscope is positioned at the beginning of the preplanned path and the real bronchoscope is positioned near the main carina;

FIG. 2B shows the global registration algorithm is invoked at generation 1 with the paths superimposed on the RB view in the CT-Video Match Tool;

FIGS. 2C-2E follow the guidance strategy at consecutive bifurcations with the physician moving the bronchoscope followed by invocation of global registration;

FIG. 2F shows that coughing leads to slippage of the bronchoscope;

FIG. 2G shows that after the coughing event has passed, the bronchoscope is positioned to view the nearest bifurcation and global registration is invoked to identify the exact position of the bronchoscope;

FIG. 2H shows that during the localization phase, the ROI is superimposed on the RB view for the physician's reference after local registration is invoked;

FIG. 4A shows the airway trees for the two phantom cases with the ROI lying at the end of the right intermediate bronchus at airway generation 3 for phantom 1;

FIG. 4B shows airway trees for the two phantom cases with the ROI lying inside the right lung at airway generation 7 for phantom 2;

FIGS. 5A-5D depict the system display during image-guided bronchoscopy to an ROI; specifically, FIG. 5A shows the virtual bronchoscope and the real bronchoscope are positioned at the main carina at generation 1. The maneuvers to be followed are shown on the guidance dialog and the first generation is highlighted in the thumbnail visualization tool;

FIGS. 5B-5D depict the visualization tools at airway generations 2, 6 and 7, respectively. At generation 7, the ROI is displayed for localization.

DETAILED DESCRIPTION OF THE INVENTION

Figure 1A:
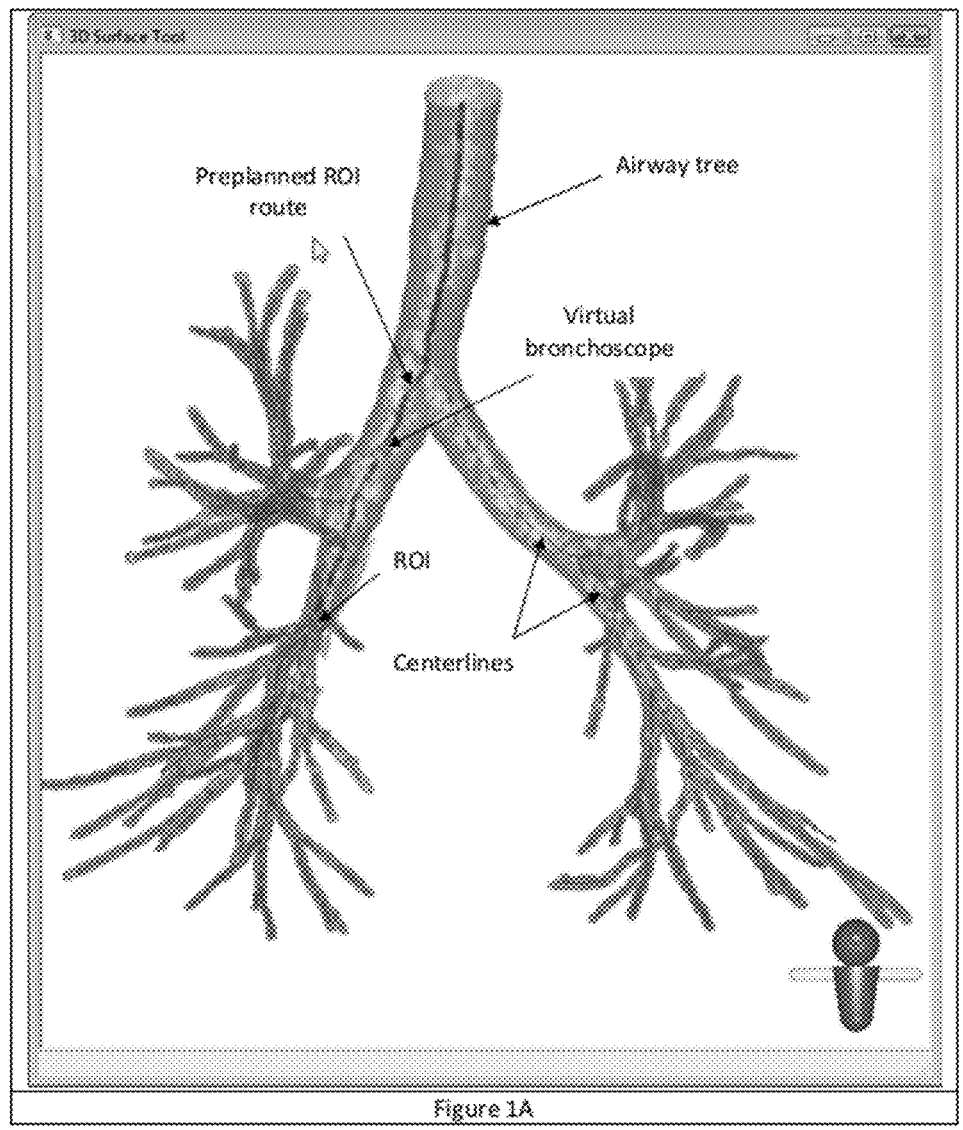

The work flow of our image-based bronchoscopy system involves two stages [13,14]: 1) procedure planning; and 2) guided bronchoscopy. During procedure planning, the patient's 3D MDCT chest scan serves as the input. The physician identifies the 3D ROIs in the scan. Next, automated analysis processes the MDCT data to segment the airway tree, compute airway centerlines and define the interior and exterior airway surfaces [23, 24]. In addition, the optimal airway centerline path is identified for later navigation to each ROI. Using the surfaces, it is possible to render VB views from any arbitrary view point $\theta=(x, y, z, \alpha, \beta, \gamma)$, where $(x, y, z)$ give the 3D spatial position and $(\alpha, \beta, \gamma)$ specify the Euler angles. We denote the VB views by $I_{CT}(\theta)$. Thus, the outputs of the planning stage are: 1) 3D ROIs; 2) interior and exterior surfaces for the segmented airway tree; 3) centerline paths; and 4) a planned path to each ROI. These data abstractions constitute the Virtual World.

During guided bronchoscopy, RB endoluminal video frames, denoted by $I_V$, are continuously obtained from the bronchoscope. Three visualization tools and a guidance dialog, presented by the guidance computer, serve to guide the physician, as shown in FIG. 1. These tools are summarized below:

1. The 3D Surface Tool (FIG. 1A) depicts the segmented airway tree, centerlines, preplanned ROI route, and the global position of the virtual bronchoscope in the airway tree [14,15]. While the disclosed colors are used in one implemented embodiment, the invention is not limited in this regard insofar as other colors and B/W designations may be used depending upon available printing and/or display apparatus.

2. The CT-Video Match Tool (FIG. 1B) comprises two sections. The top section displays VB views side-by-side with the live RB frames. In this section, it is possible to overlay a guidance route onto the RB frames to guide the physician [15]. The bottom section displays a "frozen" view of the VB and RB views from the most recently navigated airway bifurcation and helps partially with final ROI localization.

3. The Thumbnail Tool (FIG. 1C) is similar to that used by Asano et al [18-21]. However, unlike the static views presented in their system, we use dynamic thumbnails incorporating preplanned bronchoscope maneuvers. This tool depicts two sets of VB views at all encountered bifurcations along the complete preplanned route for an ROI, with the correct route highlighted for each bifurcation and incorrect routes. In each pair of views, the top VB view depicts the bifurcation as seen when the bifurcation is approached by the bronchoscope, while the bottom VB view depicts the bifurcation after the bronchoscope has been rotated as per preplanned guidance instructions. Also, during bronchoscopy, this tool highlights the current bifurcation by an enclosing box.

4. The Guidance Dialog (FIG. 1D) suggests to the physician the proper bronchoscope maneuver to make at each encountered bifurcation along an ROI's route.

During live bronchoscopy, these tools work in synchrony. Furthermore, both the Global-Registration and the Semi-Global Strategies employ them. A detailed description of these strategies appears below.

Global-Registration Strategy

The Global-Registration Strategy uses the RB frames and VB views to register the position of the bronchoscope in the 3D MDCT space and subsequently convey bronchoscopy navigation directions toward the selected ROI. This strategy employs a global-registration algorithm to establish the current bronchoscope position in 3D MDCT virtual space [22].

Given a current RB frame $I_V$ during bronchoscopy, the global-registration algorithm searches through all viewing positions $\theta \in K_{tree}$, where $K_{tree}$ includes all branches of the Virtual-World search space. This occurs in a two-step process. First, $I_V$ is used to determine the best view point at each branch of the search space. Subsequently, the VB view at the best view point for each branch is compared with $I_V$ using a weighted normalized sum-of-square error metric, and the branch whose VB view gives the optimal value is identified as the bronchoscope's current branch position. Previous work has shown that the global registration algorithm's accuracy and speed improve with search-space reduction [22]. Keeping these limitations of the global-registration algorithm in mind, we have designed a system-level guidance strategy for use during live bronchoscopy.

During live bronchoscopy, the physician maneuvers the bronchoscope to the pre-defined ROIs. A maneuver might get interrupted by episodes of patient coughing and other adverse events (e.g., the bronchoscope bumps into wall, electrical interference corrupts the video briefly) [25]. Thus, guided bronchoscopy can be considered to be broadly made up of two possible situations: 1) general guidance; and 2) adverse event.

During general guidance, the system guides the physician toward the selected ROI. Navigation guidance is provided at each bifurcation along the route to avoid faulty maneuvers. However, sometimes the physician is forced to make maneuvers spanning two or more bifurcations. Such maneuvers increase the possibility of making wrong turns. However, if the search space of the global-registration algorithm includes all branches that lie within at least two generations of the last registered position, then the faulty maneuver can be detected and guidance instructions for bringing the bronchoscope back on the correct path can be given. Furthermore, the global-registration algorithm can immediately identify the bronchoscope's current position in a branch. Because of this capability, the overall system no longer requires a technician to closely follow the movements of the real bronchoscope.

During adverse events, the bronchoscope RB frames are typically useless and guidance must briefly halt until the event passes. In such an event, the bronchoscope may slip from its last registered position and move into nearby branches. However, in the absence of active maneuvering by the physician, the bronchoscope will not migrate far from the last registered position, because the bronchoscope tends to stay relatively anchored in place in the chest. Thus, for example, it is unlikely for the bronchoscope to move from one lung to the next. Therefore, after an adverse event, the bronchoscope lies conservatively within 3-4 airway generations of the last registered position and, most likely, it is closer than this to the last registered position. By including these branches in a limited search space, the global registration algorithm can identify the bronchoscope position and, thus, recover from the adverse event.

The computer display of the guidance system used by the Global-Registration Strategy employs the tools discussed earlier (FIG. 1). During bronchoscopy, the CT-Video Match Tool serves as the primary guidance tool and invokes global registration for establishing bronchoscope position. The 3D Surface Tool depicts the current global position of the bronchoscope in the airway tree, while the Thumbnail Tool depicts the expected views at each bifurcation along the preplanned ROI route. The Guidance Dialog computes the future bronchoscope maneuvers based on the output of the global registration algorithm and accordingly suggests simple navigational instructions.

Figure 2A:
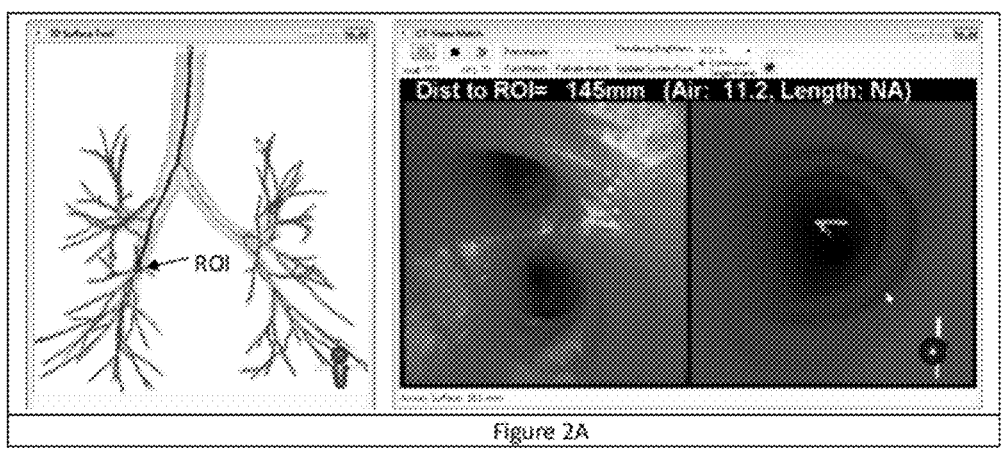
FIGS. 2A-2H show global-registration strategy results for airway phantom; specifically.

With this basic setup, the Global-Registration Strategy runs as follows:

1. During initialization, the virtual bronchoscope is positioned at the beginning of the selected ROI's optimal path, and the physician positions the bronchoscope in the main carina so that it depicts a complete view of the lumen region within the RB frame (FIG. 2A).

2. If an adverse event occurs then:
  a) The physician holds the bronchoscope steady until the adverse event passes.
  b) The physician moves the bronchoscope to a nearby bifurcation so that the bronchoscopic video depicts a complete view of the lumen region.
  c) The search space of the global registration algorithm is increased to include four airway generations about the last registered position.

Otherwise, the search space of the global registration algorithm is modified to include two airway generations about the last registered position.

Figure 2B:
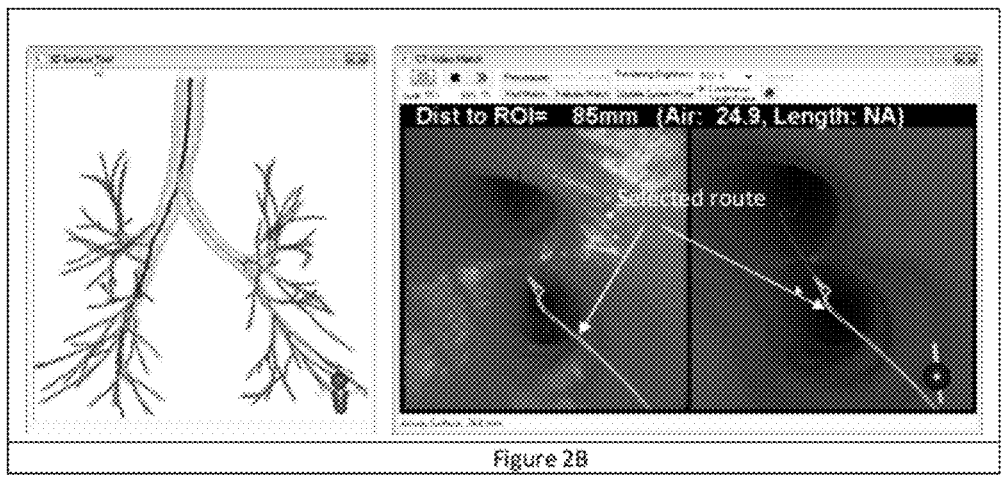
Figure 2C:
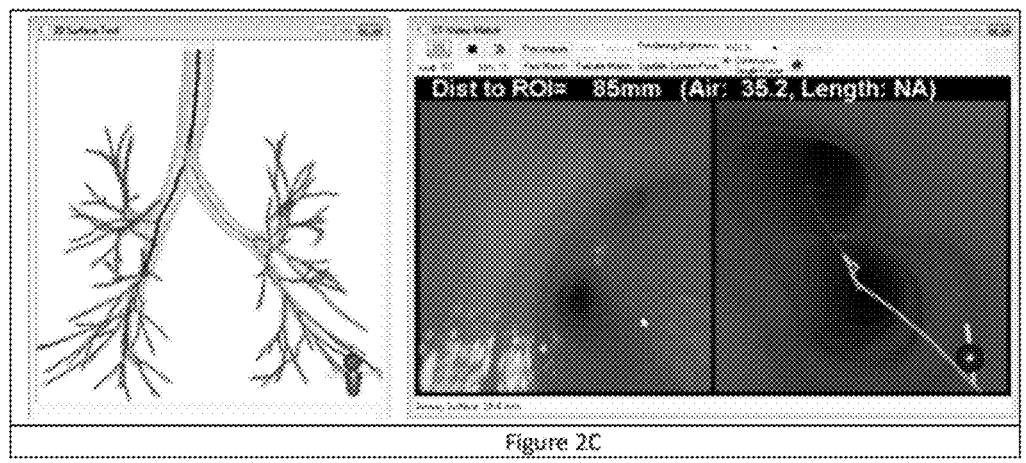
Figure 2D:
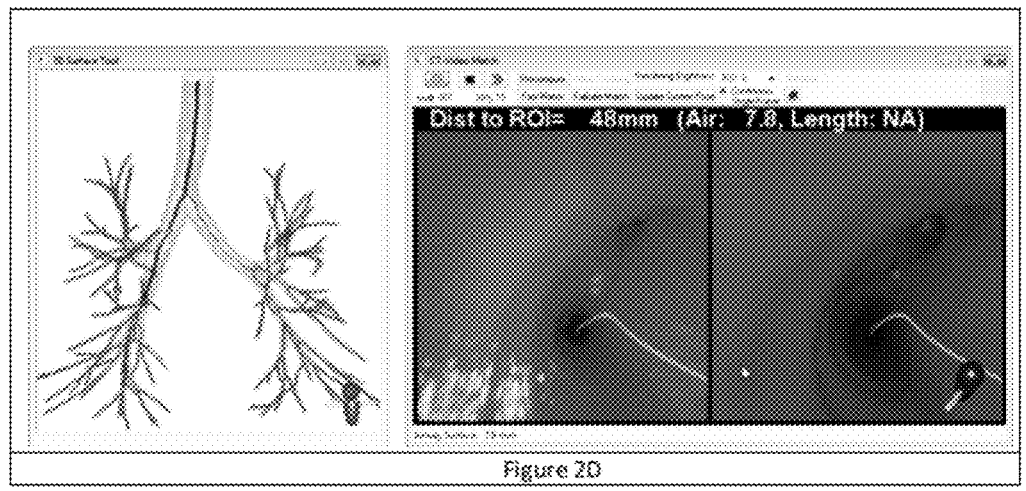
Figure 2E:
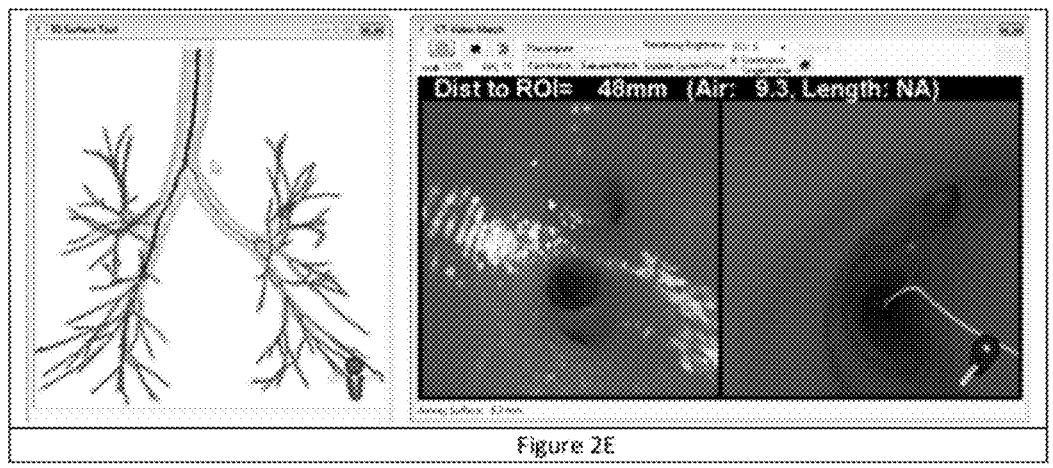

3. The physician invokes global registration by pressing a switch on a system foot pedal. This synchronizes the positions of the real and virtual bronchoscopes. Subsequently, there are three possibilities:
  a) Global registration is correct and the bronchoscope is on the correct path: In the CT-Video Match Tool, the paths are superimposed on the RB frame. The selected route (FIG. 2B) serves as a guide to the physician along the correct path to the next generation. The Guidance Dialog displays "Move forward," indicating that the physician should move the bronchoscope forward by one generation along the path.
  b) Global registration is correct and the bronchoscope is not on the correct path: In the CT-Video Match Tool, the paths are superimposed on the RB frame. The absence of the selected route indicates that the bronchoscope is not on the correct path. The Guidance Dialog displays "Fall back N generations", where 'N' indicates the number of airway generations needed to pull the bronchoscope back onto the correct path.
  c) Global registration is incorrect: The physician presses a switch on the foot pedal, which causes the virtual bronchoscope to return to its previous position.

4. Depending on the result of the global-registration algorithm in the previous step, the physician maneuvers the bronchoscope in one of three different ways:
  a) Global registration is correct and the bronchoscope is on the correct path: The physician advances the bronchoscope by one airway generation along the indicated path.
  b) Global registration is correct and the bronchoscope is not on the correct path: The physician pulls back the bronchoscope by 'N' airway generations to return back to the correct path.
  c) Global registration is incorrect: The physician holds the bronchoscope steady at the current bifurcation.

In each of the above cases, the physician should position the bronchoscope so that the RB video frames depict a complete view of the lumen region.

5. Steps 2 through 4 are repeated until the general ROI vicinity is reached, generally less than 40 mm from the ROI and within the last navigable airway to the ROI's sampling site.

6. Once in the vicinity of the ROI, local registration is invoked to synchronize the positions of the virtual and the real bronchoscopes. The ROI is superimposed on the RB frame along with a graphical arrow for localization. This enhanced view is then frozen for the physician's reference [15].

Semi-Global Strategy

The Semi-Global Strategy relies on the automatically precomputed route through the airways to each ROI. These routes are computed based on the bronchoscopic and anatomical constraints in the vicinity of the ROI [23]. By incorporating the known limitations in the maneuverability of a bronchoscope, it is possible to precompute discrete feasible maneuvers of the bronchoscope at each branch along an ROI's preplanned feasible route. Using these discrete maneuvers, the Semi-Global Strategy presents a global picture of all bifurcations and their relative proper orientations along the ROI route to guide the physician. We now present the details of this strategy.

The Semi-Global Strategy relies on two ideas. Firstly, the airway tree is torsionally rigid. This feature of the airway tree was used by Bricault et al. [26] for Level-1 matching to establish the bronchoscope position. This feature implies that as long as a bronchoscope moves from one bifurcation to the next with the same initial roll angle and in-between rotation, the observed orientation of the bifurcation sub-division walls for the two bifurcations does not change. Furthermore, the relative sub-division wall orientations are not affected by coughing.

Figure 1B:
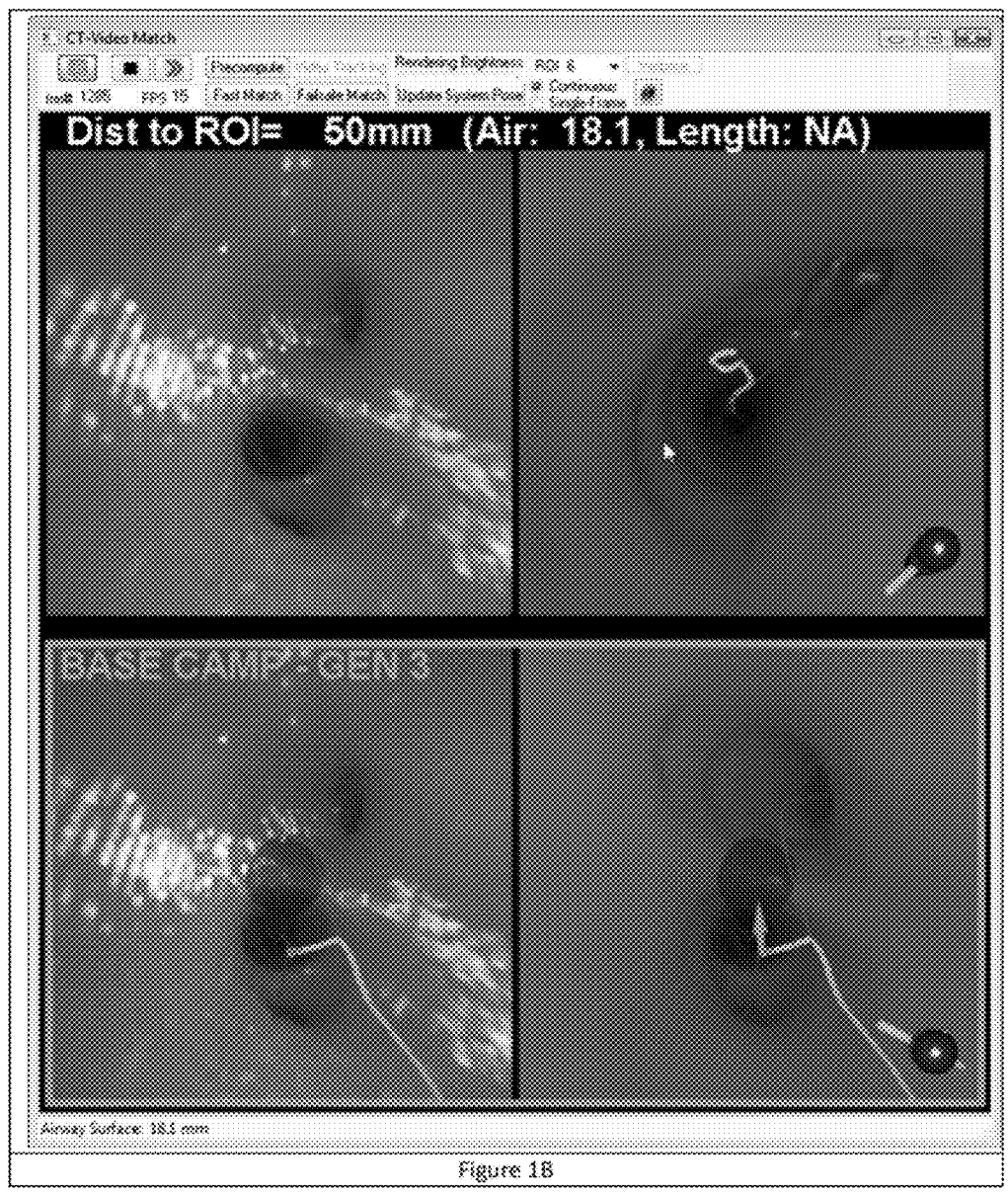
Figure 1C:
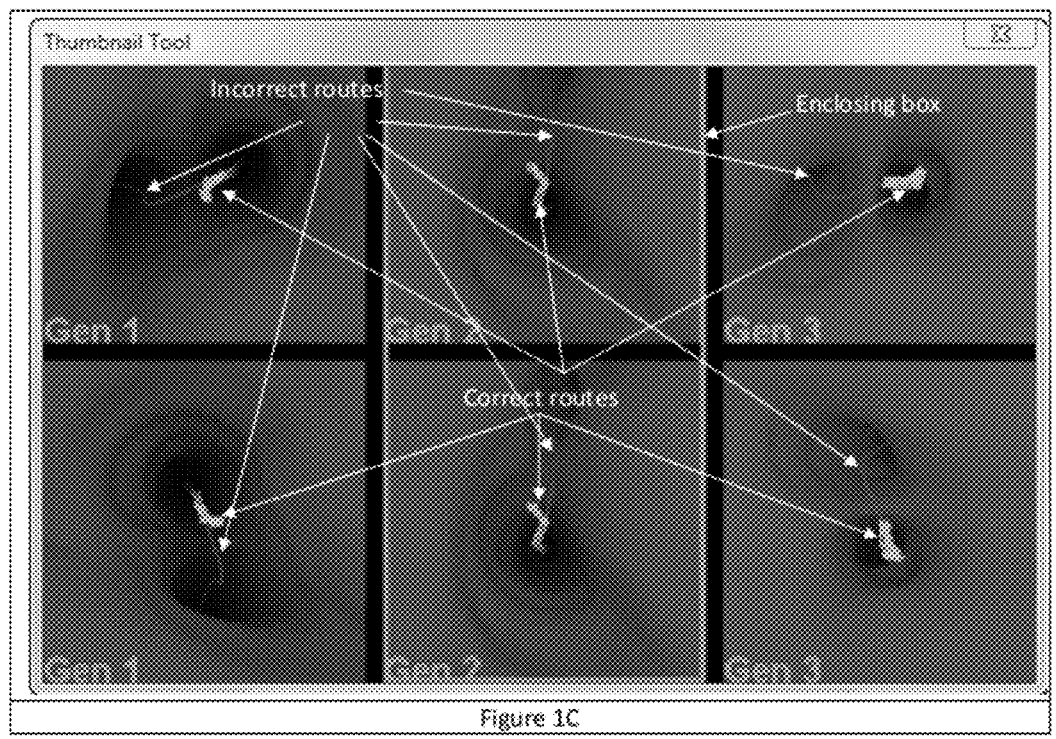
Figure 10:
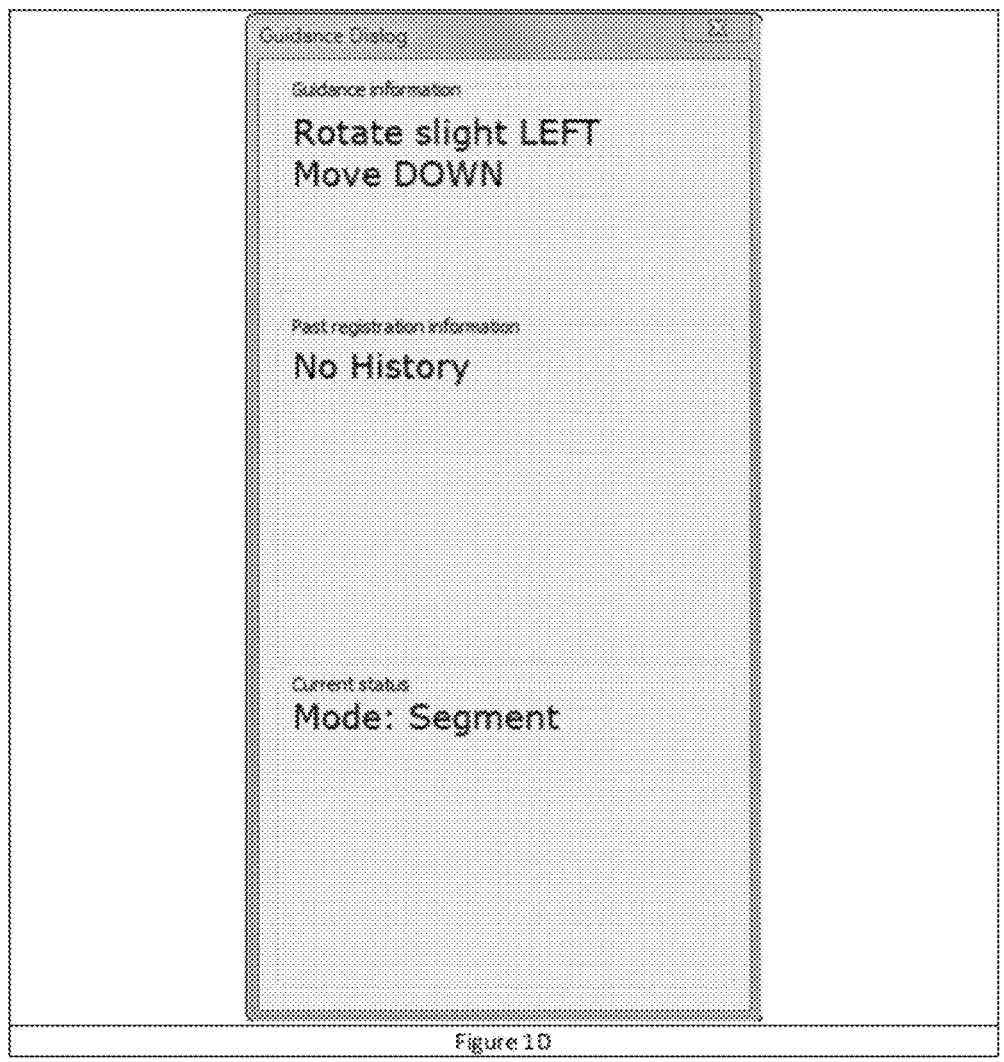

Secondly, a bronchoscope's physical dimensions and mechanics limit its maneuverability. A bronchoscope enables three movement types for maneuvering through the airways: a) push/pull maneuver; b) left/right rotation; and c) up/down articulation of the bronchoscope tip. With these limitations in maneuverability, physicians rely on a standard rotate-flex-advance procedure for moving between bifurcations as depicted in FIGS. 1A-1D [27, 28].As shown in the figure, once positioned at a bifurcation, a bronchoscope cannot be moved laterally to navigate to the next airway generation. Instead, the physician must rotate the bronchoscope so that the lumen region for the next branch is located at the top or bottom of the RB frame (FIGS. 1B or 1D). Subsequently, the articulated tip of the bronchoscope is moved up/down to insert it deeper into the airways along the selected route. In addition to the above-mentioned maneuverability limitation, the bronchoscope also suffers a restriction in its scope for rotation. The physician cannot rotate the bronchoscope indefinitely as the grip becomes infeasible; i.e, the physician can twist his/her wrist by a limited amount. To avoid this situation, the bronchoscope rotation is limited to ±90° from the neutral position in either direction. Considering these limitations, we draw upon Algorithm 1 for precomputing suggested bronchoscope movements (rotation and insertion) at each bifurcation along the ROI route.

Algorithm 1: Pre-computation of bronchoscope movements (rotation and insertion direction) at each bifurcation along a route.

```
input : Precomputed path to ROI with bifurcation view sites b_i, i ∈ [1,N]
output: Bronchoscope rotation and insertion direction at each bifurcation - bifurcationRotationAngle_i
        and bifurcationInsertionMotion_i ∀i ∈ [1,N]
Set rotation Angle = 0;
for all b_i, i ∈ [1,N] do
 |  Render I_CT at b_i;
 |  Compute angle θ (θ ∈ [−90,270]) made by line joining the center of image I_CT with the center
 |  of the lumen region of the next branch with the positive x-axis;
 |  if θ > −90 AND θ < 90 then              // lumen region lies in first or fourth quadrant
 |   |  θ_1 = θ + 90;
 |   |  θ_2 = 90 − θ;
 |   |  insertionValue = 1;
 |  else if θ > 90 AND θ < 270 then          // lumen region lies in second or third quadrant
 |   |  θ_1 = θ − 90;
 |   |  θ_2 = 270 − θ;
 |   |  insertionValue = 2;
 |  ⌊
 |  if rotationAngle − θ_1 > −90 then                      // counterclockwise rotation
 |   |  bifurcationRotationAngle_i = −θ_1;
 |   |  rotationAngle = rotationAngle − θ_1;
 |   |  if insertionValue == 1 then                       // move articulating tip down
 |   |   |  bifurcationInsertionMotion_i = Down;
 |   |  else                                              // move articulating tip upwards
 |   |   |  bifurcationInsertionMotion_i = Up;
 |   |  ⌊
 |  else                                                  // clockwise rotation
 |   |  bifurcationRotationAngle_i = θ_2;
 |   |  rotationAngle = rotationAngle + θ_2;
 |   |  if insertionValue == 1 then                       // move articulating tip upwards
 |   |   |  bifurcationInsertionMotion_i = Up;
 |   |  else                                              // move articulating tip downwards
 |   |   |  bifurcationInsertionMotion_i = Down;
 |   |  ⌊
 |  ⌊
⌊
Return bifurcationRotationAngle_i and bifurcationInsertionMotion_i ∀i ∈ [1,N];
```

By combining the precomputed bronchoscope movements along with the expected VB views at each bifurcation along an ROI route, the rigid 3D structure of the airway tree is conveyed, thus guiding the physician along the correct route. The computer display for the Semi-Global Strategy again uses the tools shown in FIGS. 1A-1D. Here, the CT-Video Match Tool depicts the RB frames and the VB views for guiding the physician in its top section. The bottom section is used during the localization phase at the end of guidance. The 3D Surface Tool depicts the global bronchoscope position in the airway tree, while the Thumbnail Tool depicts all the bifurcation views along the ROI route. The Guidance Dialog suggests the bronchoscope rotation and the motion of the articulating tip. The bronchoscope rotation movement is one of the following: a) rotate right; b) rotate left; c) rotate slight (<30°) right; d) rotate slight (<30°) left; or e) no rotation (blank). Possible motions of the articulating tip are as follows: a) move up; or b) move down.

The Semi-Global Strategy shares many of the same elements as the Global-Registration Strategy as described below:

1. During initialization, the virtual bronchoscope is positioned at the main carina at the beginning of the selected ROI's optimal path and the physician positions the bronchoscope in the main carina so that it depicts a complete view of the lumen region within the RB frame.

2. The subsequent bronchoscope maneuvers are displayed on the Guidance Dialog. The physician presses a switch on the system foot pedal and the VB view presents an animation displaying the suggested rotation and insertion of the bronchoscope to move to the next bifurcation.

3. In case an adverse event occurs:

a) The physician holds the bronchoscope steady until the adverse event passes.

b) The physician moves the bronchoscope to a nearby bifurcation so that the bronchoscopic video depicts a complete view of the lumen region. The search space of the global registration algorithm is increased to include four airway generations about the last bifurcation. Global registration is invoked to establish the current bronchoscope position. The maneuvers suggested on the Guidance Dialog are followed to move back to the correct route and step 2 is repeated.

Otherwise, step 4 is executed.

4. The physician mimics the VB animated maneuver using the real bronchoscope and moves to the next bifurcation. Optionally, the global registration algorithm can be invoked to confium the bronchoscope position.

5. Steps 2 through 4 are repeated until the general ROI vicinity is reached.

6. Once in the vicinity of the ROI, local registration is invoked to synchronize the positions of the virtual and the real bronchoscopes. The ROI is superimposed on the RB view along with a graphical arrow for localization. The view is then frozen for the physician's reference [15].

Method Comments and System Implementation

In either strategy, when the global-registration algorithm is invoked, the size of the search space, $K_{tree}$, is varied depending on the situation. Currently, the size of the search space is user-defined and set as a default to two airway generations about the previously registered position in general situations and four airway generations in case of adverse events. The search space is also isolated by lung. Thus, for example, if the previous registered position was at the second airway generation in the right lung, subsequent search spaces for the global registration algorithm will not include any branches from the left lung. If global-registration algorithm fails during navigation for either strategy, the physician can move back to the previous position and re-invoke global registration. Upon successful global registration, guidance again can then proceed forward along the desired path. However, in the case of repeated failures, guidance can be restarted by moving the bronchoscope back to the main carina and the Semi-Global Strategy can be used as the fail-safe method for guiding the physician.

Both strategies were incorporated into a system under development by our group for image-guided bronchoscopy [13-15,23,24]. This Visual C++ software package was compiled in Visual Studio 2008 as a 64-bit executable. The software was compiled and executed on a Dell T5400 workstation with a 3GHz quad-core Xeon processor with 16 GB RAM and a 768MB NVidia graphics card. The guidance computer was interfaced to the bronchoscope by using a Matrox Solios eA frame-grabber card. Furthermore, a triple-action programmable USB foot pedal from Kinesis Corporation, commonly used for repetitive tasks such as transcription, is proposed as an interface to the guidance system; the system keyboard can also give the functionality of the foot pedal.

Results

Validation results for both system-level guidance strategies are discussed below. The Global-Registration Strategy was tested on a phantom as well as video obtained from bronchoscopic exploration of consented patients, while the Semi-Global Strategy was tested using a phantom airway tree.

Phantom Studies

Phantom studies involve applying a system-level strategy to a realistic phantom model of a human airway tree. For the phantom study, red ABS rapid plastic prototypes were created from the airway surfaces obtained from two 3D MDCT scans of consented human patients as described in Table I [15]. An Olympus BF Type 1T240 bronchoscope with distal diameter 6 mm was used for the airway exploration.

TABLE I

Phantom case study specifications.

| Phantom # | Case # | Scanner | Image Dimensions (Z × X × Y) | Resolution (Δx, Δy, Δz) in mm |
|---|---|---|---|---|
| 1 | 21405.3a | Siemens Sensation-16 | 706 × 512 × 512 | (0.67, 0.67, 0.5) |
| 2 | 20349.3.48 | Phillips Gemini TF | 373 × 512 × 512 | (0.7, 0.7, 0.8) |

Figure 2F:
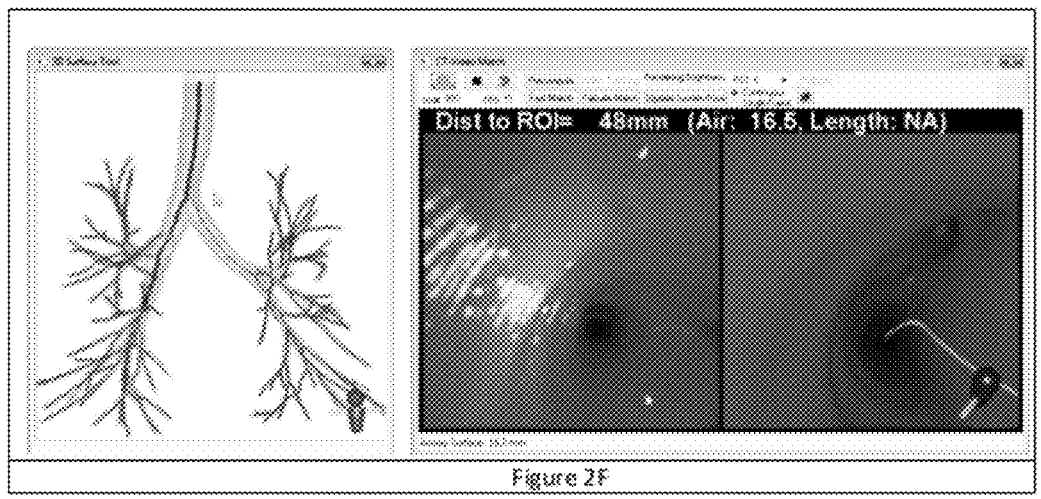
Figure 2G:
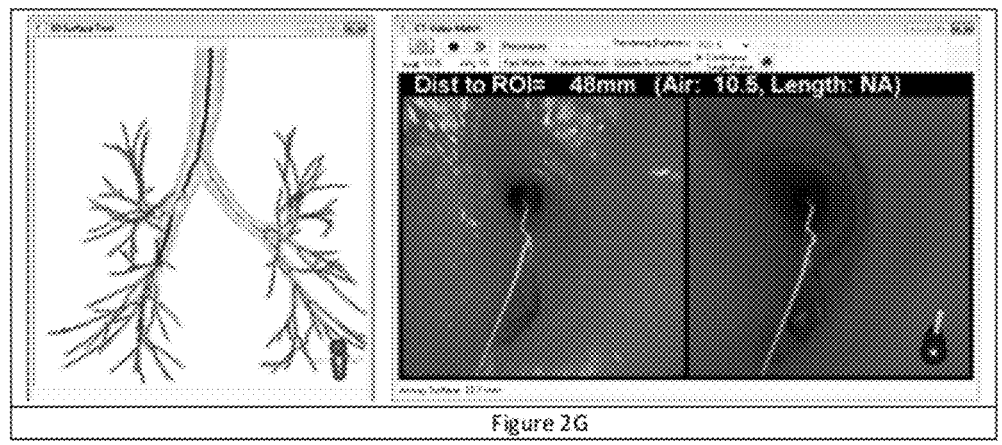
Figure 2H:
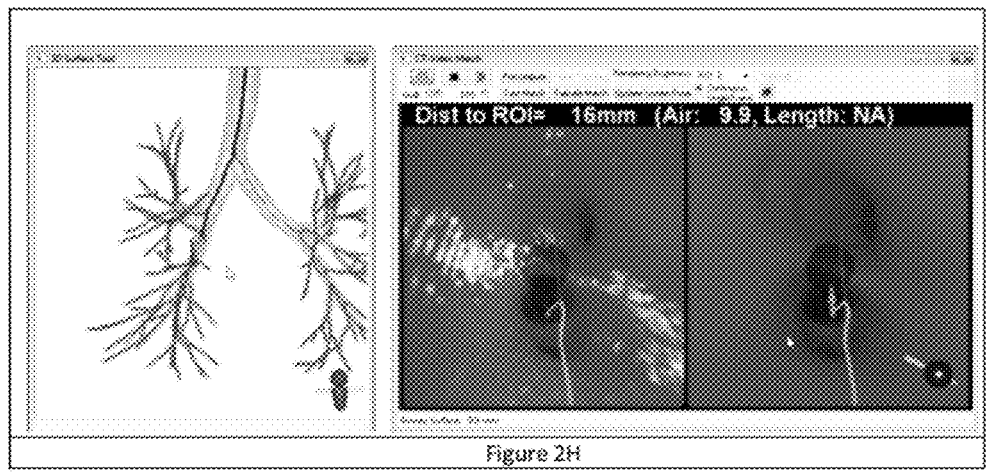
Figure 3:
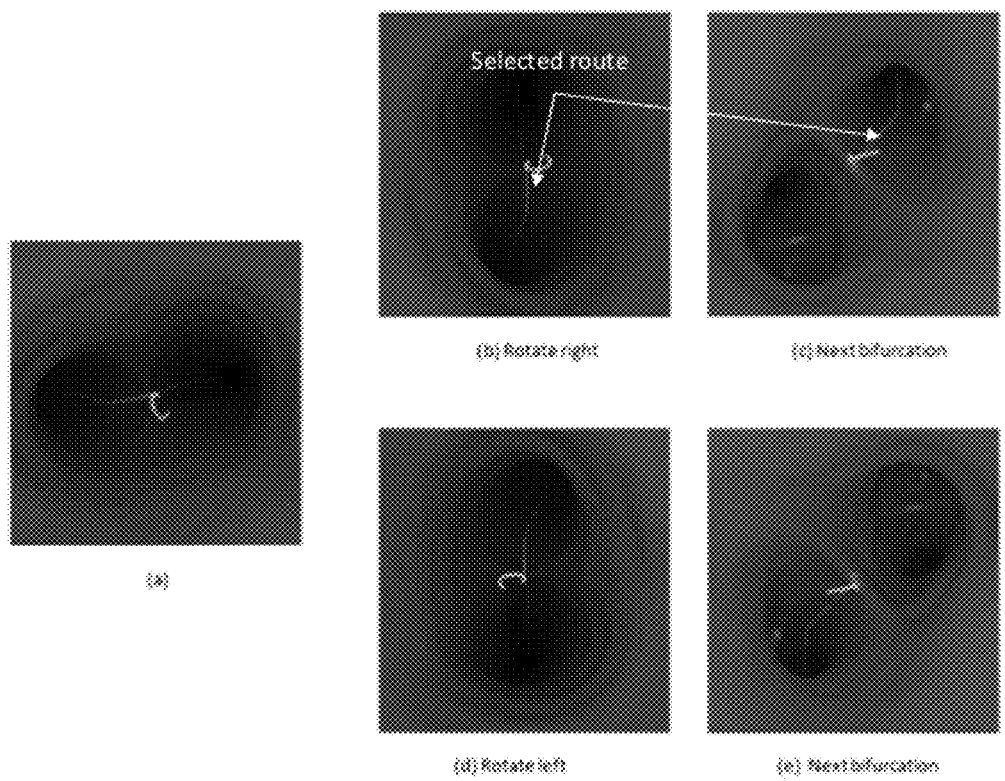
FIG. 3 shows possible bronchoscope maneuvers at a bifurcation, based on the standard rotate-flex-advance bronchoscopy technique [27, 28]. A bronchoscope maneuver from one bifurcation to the next bifurcation along a selected route is depicted. When a bronchoscope reaches a particular bifurcation (view a), there are two possible ways for maneuvering it: rotate right (view b) or rotate left (view d). By rotating the bronchoscope to the right (clock-wise) the selected route is positioned at the bottom, so that the bronchoscope tip can be articulated accordingly and the bronchoscope moved to the next bifurcation to present the bifurcation view as shown in (view c). By rotating the bronchoscope to the left (counter-clockwise), the maneuver proceeds as shown in (view d) and (view e)
Figure 4A:
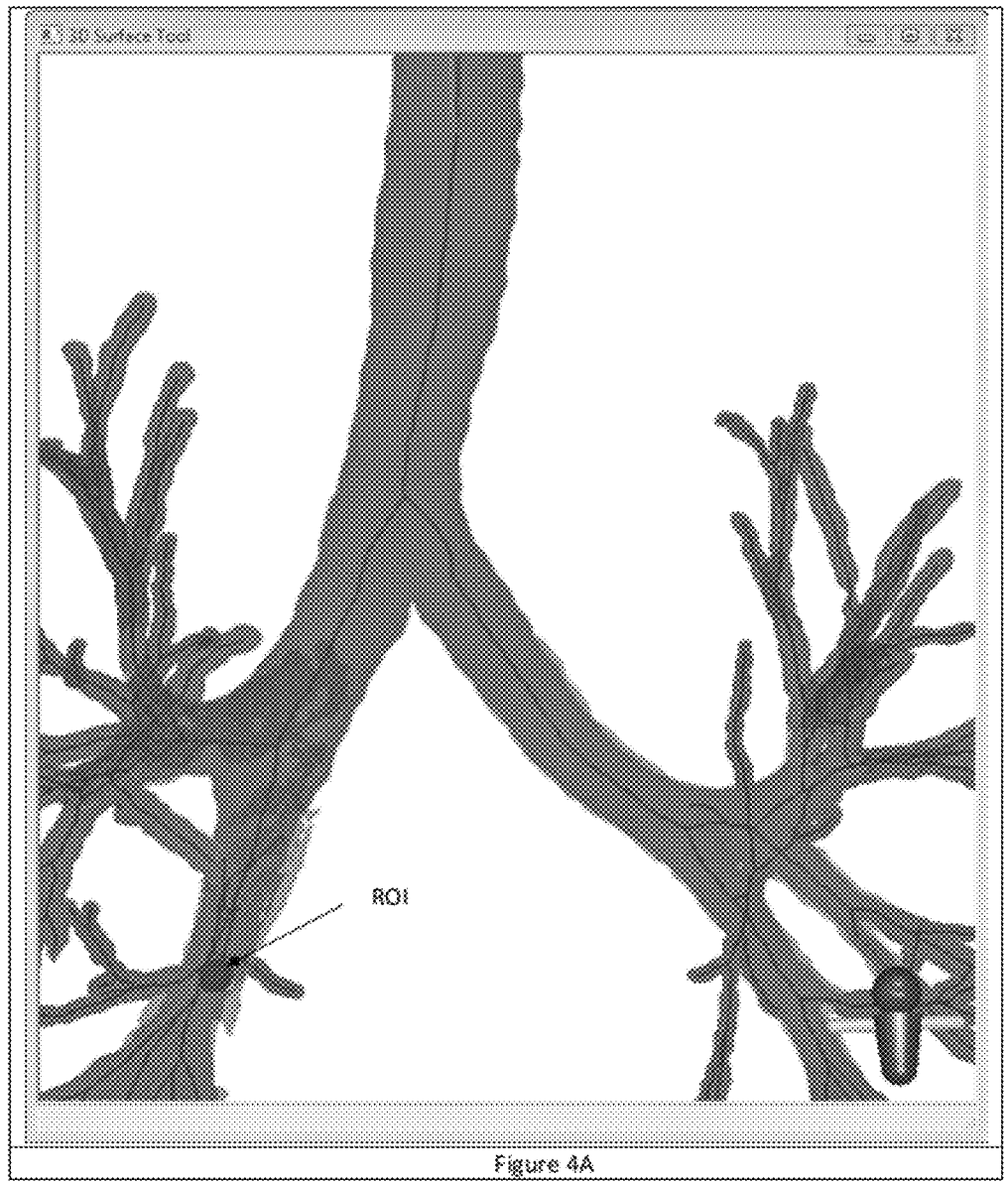
FIGS. 4A-4B show how ROIs were defined for the phantom airways; specifically.
Figure 4B:
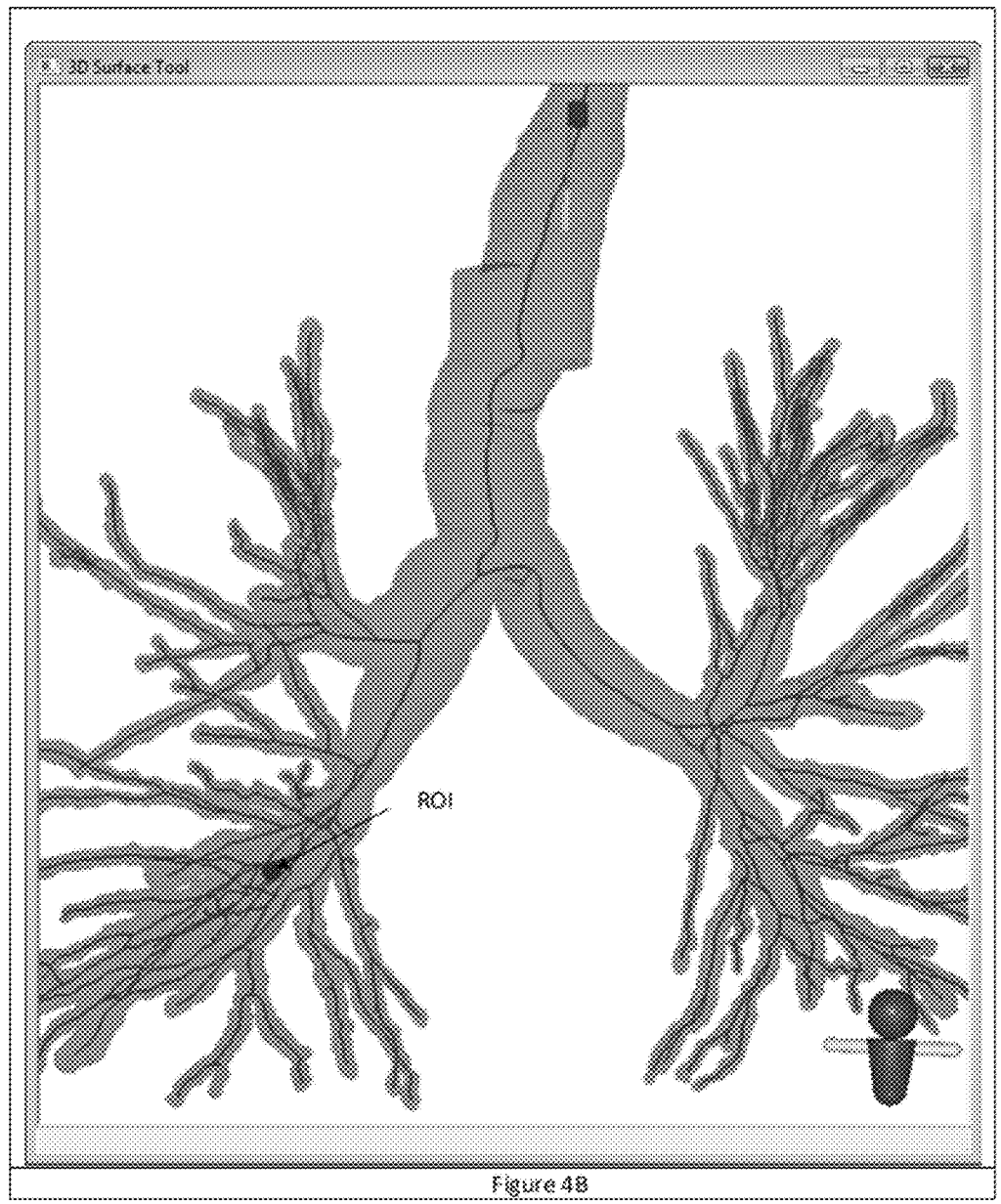
Figure 5A:
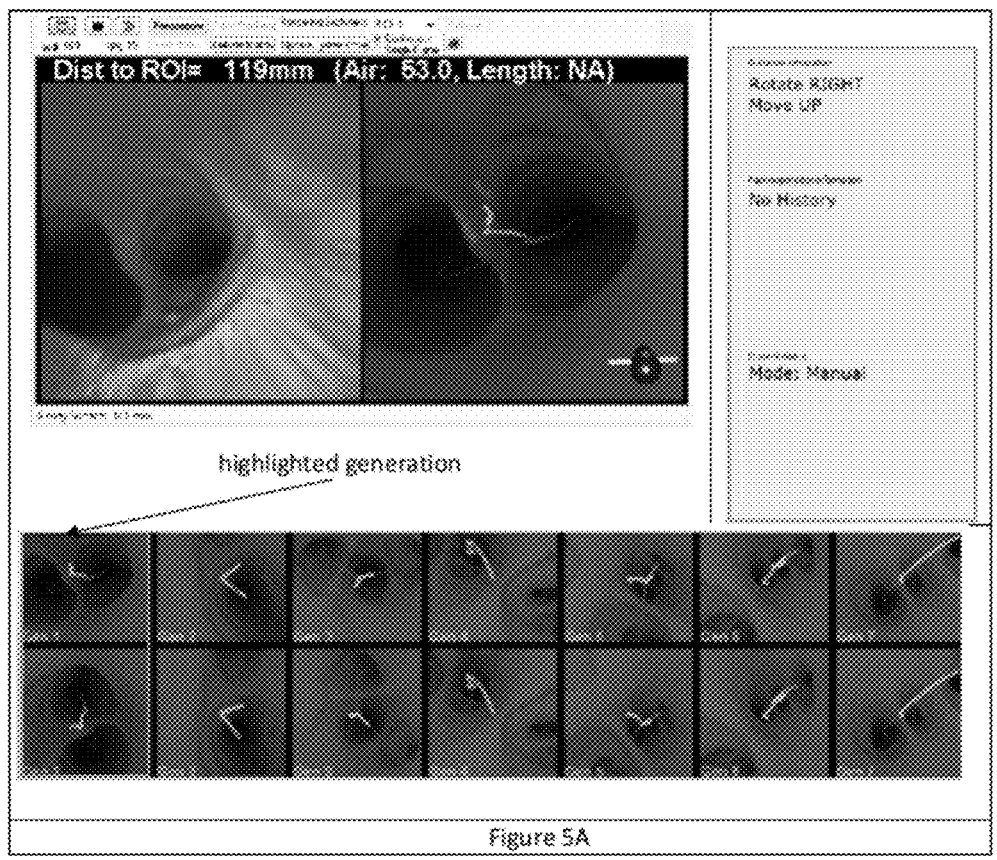
Figure 58:
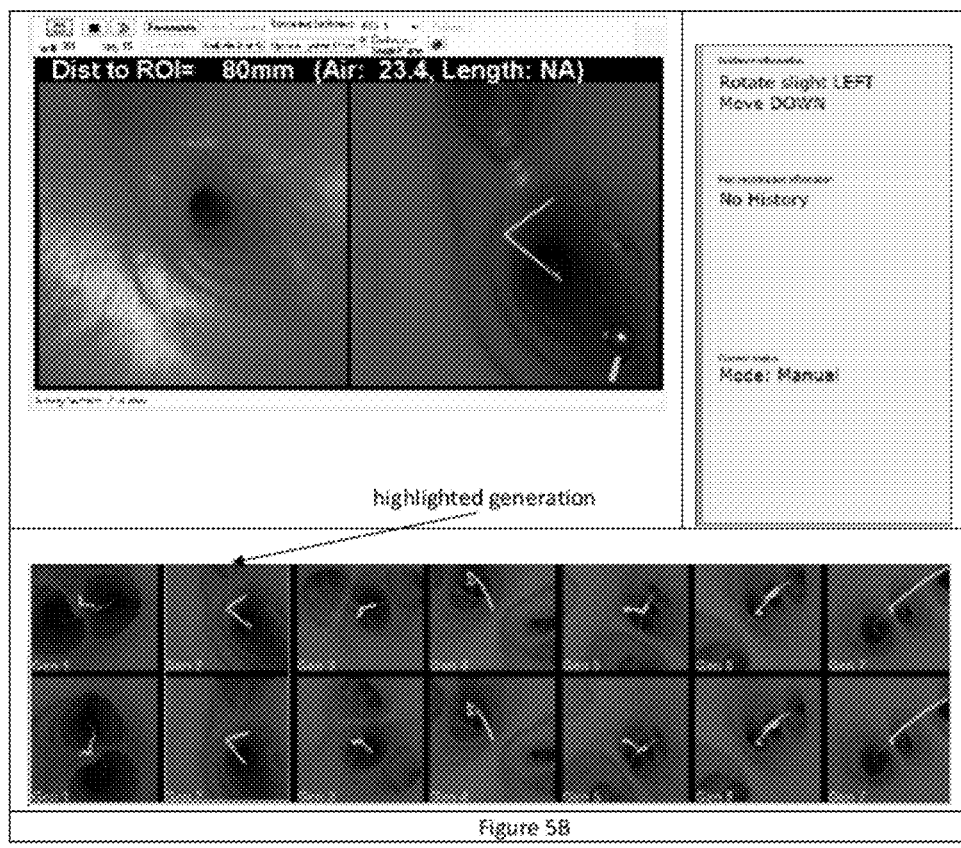
Figure 6A:
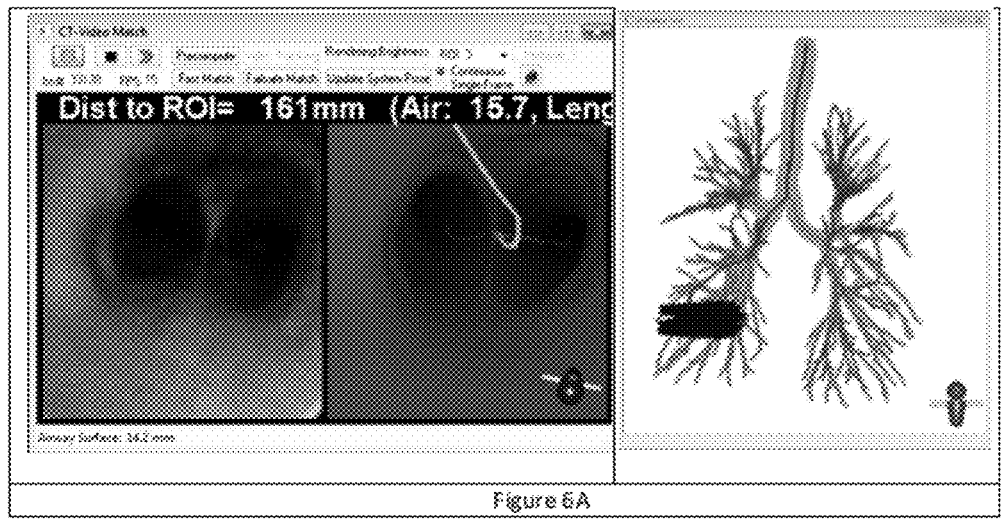
FIGS. 6A-6D show global-registration strategy results for a patient depicting the system during synchronization at airway generations 1-4 respectively.
Figure 6B:
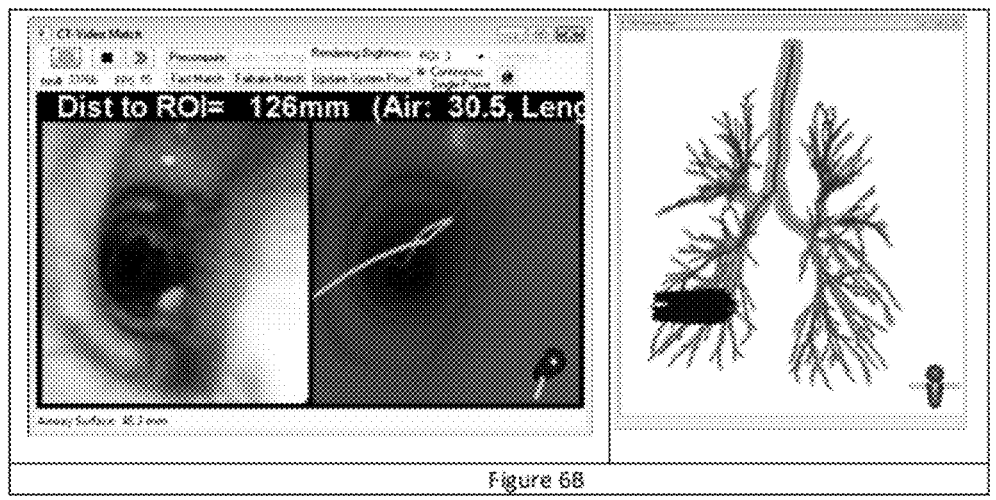
Figure 6C:
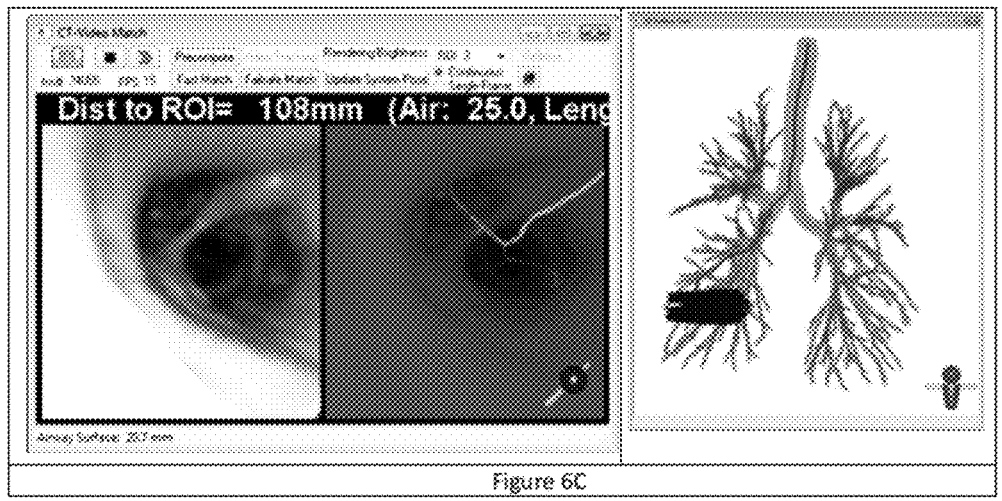
Figure 6D:
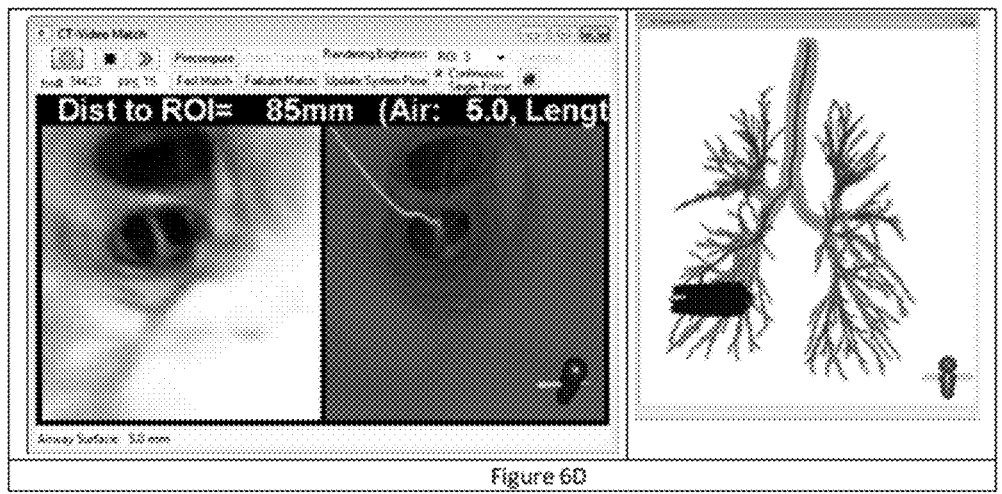

For phantom 1, a spherical ROI was manually defined at a site external to the endoluminal surface at the end of the right intermediate bronchus as shown in FIG. 4A. For phantom 2, a spherical ROI was defined in the right lung as shown in FIG. 4B. Next, automated software processed the MDCT data to segment the airway tree, compute airway centerlines and define the interior and exterior airway surfaces for the two cases[13, 23, 24]. The optimal airway centerline path was also identified for later navigation to each ROI for each case. FIGS. 2A-2H depicts the step-by-step Global-Registration Strategy to approach the ROI for Phantom 1 and also the recovery after a simulated coughing event. FIG. 2A represents the initialization stage. Figures. 2B-2E are the depictions along consecutive bifurcations toward the ROI. FIGS. 2F-2G depicts the guidance system recovering from a simulated coughing episode. FIG. 2H depicts the localization phase and a view is frozen at this stage. FIGS. 5A-5D depicts the Semi-Global Strategy in use at some bifurcations along the ROI route for Phantom 2.

The Global-Registration Strategy successfully navigated to the ROI at airway generation 3 for Phantom 1 and was also able to recover from a simulated coughing episode, while the Semi-Global Strategy successfully navigated to the end of the preplanned ROI route at airway generation 7 for Phantom 2.

Human Studies

The Global-Registration Strategy was also tested on three cases as described in Table II for which video data was collected by bronchoscope exploration of live patients. For all cases, an ultrathin bronchoscope with distal diameter 2.8 mm was used. FIGS. 6A-6D show step-by-step guidance carried out for case 20349.3.51 up to airway generation 4.

The Global-Registration Strategy successfully navigated up to airway generation 5 for cases 20349.3.51 and 20349.3.28 and up to airway generation 4 for case 20349.3.41.

TABLE II

Human case study specifications.

| Case # | Scanner | Image Dimensions (Z × X × Y) | Resolution (Δx, Δy, Δz) in mm |
|---|---|---|---|
| 20349.3.28 | Siemens Definition | 693 × 512 × 512 | (0.62, 0.62, 0.5) |
| 20349.3.41 | Siemens | 699 × 512 × 512 | (0.77, 0.77, 0.5) |
| 20349.3.51 | Siemens | 696 × 512 × 512 | (0.53, 0.53, 0.5) |

In summary, two global-registration-based strategies for image-guided bronchoscopy provide several improvements over previous system-level strategies. The Global-Registration Strategy facilitates automatic detection and correction of faulty maneuvers by the physician during bronchoscopy. Furthermore, by using this strategy the system can recover from adverse events arising from patient coughing or dynamic airway collapse. The rotation of the bronchoscope can be automatically registered without any manual intervention, and the user interface constitutes a minimal command set. Thus, this strategy facilitates a system built for direct control by the physician without any need for a technician. This strategy was used successfully in bronchoscopy guidance using airway phantoms up to airway generation 3 and could also be used for guidance using live bronchoscopic videos up to airway generation 4.

The Semi-Global Strategy is a fail-safe strategy that exploits how a bronchoscope has to be moved within the airway tree. Thus, in this strategy, feasible discrete bronchoscope maneuvers are suggested to the physician at each bifurcation. This strategy provides implicit error correction as the physician knows the expected orientation of the bifurcation at each airway generation. Furthermore, this strategy depends on the relative orientation of the bifurcation sub-division walls that are rigid and hence less susceptible to errors caused in the airway surface due to 3D MDCT resolution limits. It also has a minimal command set, thus allowing the system to be directly controlled by a physician using a foot pedal. In validation testing, this strategy enabled guidance on a human phantom airway to the end of the preplanned ROI route up to airway generation 7.

REFERENCES

[1] A. Jemal and R. Siegel and E. Ward and Y. Hao and J. Xu and M. J. Thun. Cancer statistics, 2009. *CA Cancer J. Clin.*, 59(4):225-249, 2009.

[2] K. P. Wang and A. C. Mehta and J. F. Turner, eds., *Flexible Bronchoscopy*. Blackwell Publishing, Cambridge, MA, 2 edition, 2003.

[3] A. D. Sihoe and A. P. Yim. Lung cancer staging. *J. Surgical Research*, 117(1):92-106,2004.

[4] H Minami and Y Ando and F Nomura and S Sakai and K Shimokata. Interbronchoscopist variability in the diagnosis of lung cancer by flexible bronchoscopy. *Chest*, 105(2):1658-1662,1994.

[5] M. Y. Dolina and D. C. Cornish and S. A. Merritt and L. Rai and R. Mahraj and W. E. Higgins and R. Bascom. Interbronchoscopist variability in endobronchial path selection: a simulation study. *Chest*, 133(4):897-905, 2008.

[6] S. B. Solomon and P. White, Jr. and C. M. Wiener and J. B. Orens and K. P. Wang. Three-dimensionsal CT-guided bronchoscopy with a real-time electromagnetic position sensor: a comparison of two image registration methods. *Chest*, 118(6):1783-1787, 2000.

[7] K. Hopper and T. Lucas and K. Gleeson and J. Stauffer and R. Bascom and D. Mauger and R. Mahraj. Transbronchial biopsy with virtual CT bronchoscopy and nodal highlighting. *Radiology*, 221(2):531-536, 2001.

[8] Y. Schwarz and J. Greif and H. D. Becker and A. Ernst and A. Mehta. Real-time electromagnetic navigation bronchoscopy to peripheral lung lesions using overlaid CT images: the first human study. *Chest*, 129(4):988-994, 2006.

[9] H. D. Becker and F. Herth and A. Ernst and Y. Schwarz. Bronchoscopic biopsy of peripheral lung lesions under electromagnetic guidance: A pilot study. *J Bronchology*, 12(1):9-13, 2005.

[10] T. R. Gildea and P. J. Mazzone and D. Karnak and M. Meziane and A. C. Mehta. Electromagnetic navigation diagnostic bronchoscopy: a prospective study. *Am. J. Resp. Crit. Care Med.*, 174(9):982-989, 2006.

[11] Wegner, I. and Biederer, J. and Tetzlaff, R. and Wolf, I. and Meinzer, H.-P. Evaluation and extension of a navigation system for bronchoscopy inside human lungs. In Cleary, Kevin R. and Miga, Michael I., editors, *SPIE Medical Imaging 2007: Visualization and Image-Guided Procedures*, pages 65091H1-65091H12, 2007.

[12] K. Mori and K. Ishitani and D. Deguchi and T. Kitasaka and Y. Suenaga and H. Takabatake and M. Mori and H. Natori. Compensation of electromagnetic tracking system using an optical tracker and its application to bronchoscopy navigation system. In Kevin R. Cleary and Michael I. Miga, editors, number 1, pages 65090M, 2007. SPIE.

[13] J. P. Helferty and A. J. Sherbondy and A. P. Kiraly and W. E. Higgins. Computer-based system for the virtual-endoscopic guidance of bronchoscopy. *Comput. Vis. Image Underst.*, 108(1-2):171-187, 2007.

[14] W. E. Higgins and J. P. Helferty and K. Lu and S. A. Merritt and L. Rai and K. C. Yu. 3D CT-video fusion for image-guided bronchoscopy. *Comput. Med. Imaging Graph.*, 32(3):159-173, 2008.

[15] S. A. Merritt and J. D. Gibbs and K. C. Yu and V. Patel and L. Rai and D. C. Cornish and R. Bascom and W. E. Higgins. Real-Time Image-Guided Bronchoscopy for Peripheral Lung Lesions: A Phantom Study. *Chest*, 134(5):1017-1026, 2008.

[16] Soper, T. D. and Haynor, D. R. and Glenny, R. W. and Seibel, E. J. Validation of CT-video registration for guiding a novel ultrathin bronchoscope to peripheral lung nodules using electromagnetic tracking. *Society of Photo-Optical Instrumentation Engineers (SPIE) Conference Series* in Society of Photo-Optical Instrumentation Engineers (SPIE) Conference Series, 2009.

[17] H. P. McAdams and P. C. Goodman and P. Kussin. Virtual bronchoscopy for directing transbronchial needle aspiration of hilar and mediastinal lymph nodes: a pilot study. *Am. J. Roentgenology*, 170(5):1361-1364, 1998.

[18] F. Asano and Y. Matsuno and N. Shinagawa and K. Yamazaki and T. Suzuki and H. Moriya. A virtual bronchoscopic navigation system for pulmonary peripheral lesions. *Chest*, 130(2):559-66, 2006.

[19] N. Shinagawa and K. Yamazaki and Y. Onodera and F. Asano and T. Ishida and H. Moriya and M. Nishimura. Virtual bronchoscopic navigation system shortens the examination time—Feasibility study of virtual bronchoscopic navigation system. *Lung Cancer*, 56(2):201-206, 2007.

[20] F. Asano and Y. Matsuno and A. Tsuzuku and M. Anzai and N. Shinagawa and H. Moriya and others. Diagnosis of peripheral pulmonary lesions using a bronchoscope insertion guidance system combined with endobronchial ultrasonography with a guide sheath. *Lung Cancer*, 60(3):366-373, 2008.

[21] F. Asano. Virtual Bronchoscopic Navigation. *Clinics in Chest Medicine*, 31(1):75-85,2010. Interventional Pulmonology.

[22] R. Khare and W. E. Higgins. Toward image-based global registration for bronchoscopy guidance. In M. I. Miga and K. H. Wong, editors, *SPIE Medical Imaging 2010: Visualization, Image-Guided Procedures, and Modeling*, pages 762510-1-762510-12, 2010.

[23] J. D. Gibbs and M. W. Graham and W. E. Higgins. 3D MDCT-based system for planning peripheral bronchoscopic procedures. *Computers in Biology and Medicine*, 39(3):266-279,2009.

[24] M. W. Graham and J. D. Gibbs and D. C. Cornish and W. E. Higgins. Robust 3D Airway-Tree Segmentation for Image-Guided Peripheral Bronchoscopy. *IEEE Trans. Medical Imaging*, 29(4):982-997, 2010.

[25] W. E. Higgins and J. P. Helferty and D. R. Padfield. Integrated bronchoscopic video tracking and 3D CT registration for virtual bronchoscopy. *SPIE Medical Imaging 2003: Physiology and Function: Methods, Systems and Applications.*, 5031:80-89, 2003. A.V. Clough and A.A. Amini (ed.).

[26] I. Bricault and G. Ferretti and P. Cinquin. Registration of Real and CT-Derived Virtual Bronchoscopic Images to Assist Transbronchial Biopsy. *IEEE Transactions on Medical Imaging*, 17(5):703-714, 1998.

[27] Bronchoscopy Step-by-Step. an Electronic On-Line Multimedia Slide Presentation, http://www.bronchoscopy.org, 2004.

[28] S. M. Nadeem. Fiberoptic bronchoscopy: the technique. educational material from Committee for European Education in Anesthesiology, http://www.euroviane.net, 2009.

The invention claimed is:

1. A semi-global method for image-guided bronchoscopy adapted for use with a bronchoscope capable of articulation and rotation, including the steps of:

providing a processor coupled to a display device, the processor being programmed to pre-compute a route to a region of interest (ROI) within an airway tree including bifurcations along the pre-computed route;

presenting a global picture to a user of a bronchoscope one or more bifurcations along the pre-computed route to the region of interest (ROI) within the airway tree, the global picture symbolically displaying preferred bronchoscope orientations associated with each bifurcation;

providing discrete bronchoscope rotation and articulation maneuver instructions at one or more locations along the pre-computed route to guide the user of the bronchoscope to the ROI based upon the preferred bronchoscope orientations, wherein the maneuver instructions are displayed in dialog form.

2. The method of claim 1, including the step of presenting two views for every bifurcation along the route to the ROI.

3. The method of claim 2, wherein one view depicts the bifurcation as seen by the bronchoscope when that bifurcation is approached by the bronchoscope.

4. The method of claim 2, wherein one view depicts the bifurcation as seen by the bronchoscope after a suggested discrete bronchoscope maneuver is carried out.

5. The method of claim 1, including the step of using an animated sequence to suggest a bronchoscope maneuver.

6. The method of claim 1, including the step of suggesting a standard bronchoscope maneuver such as a rotate-flex-advance maneuver at a bifurcation.

7. The method of claim 1, wherein the bronchoscope has a known maneuverability limitation, and the limitation is used to detemiine discrete bronchoscope maneuvers at a bifurcation.

8. The method of claim 7, wherein the known limitation in the maneuverability of the bronchoscope includes rotation.

9. The method of claim 1, including the step of determining discrete bronchoscope maneuvers to minimize the total rotation of the bronchoscope at a bifurcation.

10. The method of claim 1, wherein user preferences for bifurcation orientations are used to determine a discrete bronchoscope maneuver at a bifurcation.

11. The method of claim 1, wherein airway tree topology is used to determine the discrete bronchoscope rotation and articulation maneuver at a bifurcation.

12. The method of claim 1, wherein branch length, orientation and airway tree topology are used to determine if bifurcations that can be skipped in conjunction with the step of presenting the global picture to guide a user.

13. The method of claim 12, including user-defined parameters to detemiine if a bifurcation may be skipped.

14. The method of claim 1, wherein the step of providing instructions comprises providing instructions at each bifurcation along the pre-computed route to the ROI.

15. The method of claim 1, wherein the the step of providing the instructions comprises computing rotate, flex, and advance maneuvers of the bronchoscope associated with a corresponding VB view at a branch junction.

16. The method of claim 15, further comprising the step of determining a global position of the bronchoscope being advanced through the airway tree, wherein the step of determining comprises using a computer-based image-processing global algorithm to register real bronchoscopic (RB) views obtained from the bronchoscope to virtual bronchoscopic (VB) views obtained from a precomputed data-set based on 3D image data.

17. The method of claim 16, further comprising the step of indicating to the user at least one of the following:
    i) a confirmation instruction that the global position is a point along the predefined route if the global position is presently along the predefined route; and
    ii) a corrective instruction in order to lead the bronchoscope towards the predefined route if the global position is presently off the predefined route.

18. The method of claim 16, wherein the step of determining a global position of the bronchoscope being advanced through the airway tree is invoked by depressing a foot pedal by a user of the bronchoscope.

19. The method of claim 16, wherein the corrective instruction includes retracting the bronchoscope to a nearby upstream airway bifurcation.

* * * * *